United States Patent
Smith et al.

(10) Patent No.: US 10,874,319 B2
(45) Date of Patent: Dec. 29, 2020

(54) ELECTROCARDIOGRAPH DISPLAY BY ANATOMICAL STRUCTURE

(71) Applicant: Medstar Health, Columbia, MD (US)

(72) Inventors: Mark S. Smith, Columbia, MD (US); Rahul Bhat, Columbia, MD (US)

(73) Assignee: MEDSTAR HEALTH, Columbia, MD (US)

( * ) Notice: Subject to any disclaimer, the term of this patent is extended or adjusted under 35 U.S.C. 154(b) by 1095 days.

(21) Appl. No.: 14/775,094

(22) PCT Filed: Mar. 13, 2014

(86) PCT No.: PCT/US2014/025791
§ 371 (c)(1),
(2) Date: Sep. 11, 2015

(87) PCT Pub. No.: WO2014/160090
PCT Pub. Date: Oct. 2, 2014

(65) Prior Publication Data
US 2016/0029913 A1 Feb. 4, 2016

Related U.S. Application Data

(60) Provisional application No. 61/931,816, filed on Jan. 27, 2014, provisional application No. 61/900,637, (Continued)

(51) Int. Cl.
*A61B 5/04* (2006.01)
*A61B 5/044* (2006.01)
(Continued)

(52) U.S. Cl.
CPC ............ *A61B 5/044* (2013.01); *A61B 5/0408* (2013.01); *A61B 5/04015* (2013.01);
(Continued)

(58) Field of Classification Search
CPC ..... A61B 5/044; A61B 5/7475; A61B 5/0408; A61B 5/7435; A61B 5/04015;
(Continued)

(56) References Cited

U.S. PATENT DOCUMENTS 5,956,013 A 9/1999 Raj et al.
6,654,631 B1 11/2003 Sahai
(Continued)

FOREIGN PATENT DOCUMENTS

WO 2008085179 A1 7/2008
WO 2011121494 A1 10/2011
WO 2012099933 A2 7/2012

OTHER PUBLICATIONS

Chiarugi et al., "ECG in Your Hands: A Multi-Vendor ECG Viewer for Personal Digital Assistants", Computers in Cardiology, 2003, 30, pp. 359-362.
(Continued)

*Primary Examiner* — Mallika D Fairchild
(74) *Attorney, Agent, or Firm* — Tarolli, Sundheim, Covell & Tummino LLP

(57) ABSTRACT

Systems and methods are provided for an electrocardiograph system. A set of electrodes is configured to detect a voltage differences between various pairs of locations on a body of a patient. A display is configured to visually represent digital signals derived from the plurality of detected voltage differences. A display interface is configured to format the digital signals for the display, such that the leads are grouped and displayed as a sequence of proper subsets or groups of the plurality of detected voltage differences. Each proper subset or lead group represents a specific anatomical structure of a heart of the patient.

9 Claims, 34 Drawing Sheets

Related U.S. Application Data filed on Nov. 6, 2013, provisional application No. 61/778,733, filed on Mar. 13, 2013.

(51) Int. Cl.

| | |
|---|---|
| *A61B 5/00* | (2006.01) |
| *A61B 5/0408* | (2006.01) |
| *A61B 5/0432* | (2006.01) |
| *A61B 5/0452* | (2006.01) |
| *A61B 5/0472* | (2006.01) |

(52) U.S. Cl.
CPC .......... *A61B 5/0432* (2013.01); *A61B 5/0472* (2013.01); *A61B 5/04525* (2013.01); *A61B 5/742* (2013.01); *A61B 5/7405* (2013.01); *A61B 5/7475* (2013.01); *A61B 5/7435* (2013.01); *G06F 2203/04803* (2013.01)

(58) Field of Classification Search
CPC . A61B 5/0432; A61B 5/04525; A61B 5/7405; A61B 5/0472; G06F 2203/04803
See application file for complete search history.

(56) References Cited

U.S. PATENT DOCUMENTS

| | | | |
|---|---|---|---|
| 2004/0051721 A1* | 3/2004 | Ramseth | G16H 40/63 345/689 |
| 2013/0165781 A1* | 6/2013 | Cardinale | A61B 5/044 600/440 |
| 2014/0019901 A1* | 1/2014 | Powell | A61B 5/0006 715/771 |

OTHER PUBLICATIONS

Hsieh et al., "The Clinical Application of a PACS-Dependent 12-Lead ECG and Image Information System in E-Medicine and Telemedicine", Journal of Digital Imaging, vol. 23, No. 4 (Aug. 2010), pp. 501-513.

International Search Report and Written Opinion for PCT/US2014/025791, dated Jan. 9, 2015, pp. 1-6.

\* cited by examiner

ELECTROCARDIOGRAPH DISPLAY BY ANATOMICAL STRUCTURE

RELATED APPLICATIONS

The present application claims priority to each of U.S. Provisional Patent Application Ser. No. 61/778,733 filed Mar. 13, 2013 entitled ELECTROCARDIOGRAPH DISPLAY BY ANATOMICAL STRUCTURE, U.S. Provisional Patent Application Ser. No. 61/900,637 filed Nov. 6, 2013 entitled ELECTROCARDIOGRAPH DISPLAY BY ANATOMICAL STRUCTURE, and U.S. Provisional Patent Application Ser. No. 61/931,816 filed Jan. 27, 2014 entitled ELECTROCARDIOGRAPH DISPLAY BY ANATOMICAL STRUCTURE. The entire contents of each of these applications are incorporated herein by reference in its entirety for all purposes.

TECHNICAL FIELD

The present invention relates generally to medical devices, and specifically to an electrocardiograph display in which the leads representing each of a plurality of anatomical structure are displayed in isolation and in which pairs of leads or collection of leads can be compared between two different electrocardiograms.

BACKGROUND

An electrocardiograph (ECG) device detects and amplifies tiny electrical changes on the skin caused when the heart muscle depolarizes during each heartbeat. At rest, each heart muscle cell has a negative charge, called the membrane potential, across its cell membrane. Decreasing this negative charge towards zero, via the influx of the positive cations, Na+ and Ca++, is called depolarization, which activates the mechanisms in the cell that cause it to contract. During each heartbeat, a healthy heart will have an orderly progression of a wave of depolarization that is triggered by the cells in the sinoatrial node, spreads out through the atrium, passes through the atrioventricular node, and then spreads all over the ventricles. Depolarization is followed by repolarization, in which the voltage returns to baseline. Depolarization and repolarization are detected as small rises and falls in the voltage between two electrodes placed on either side of the heart, which can be displayed, for example, as a wavy line either on a screen or on paper. This display reflects the overall rhythm of the heart and also relative lack of blood flow and heart muscle damage (e.g., ischemia, injury, and infarction) in different parts of the heart.

Usually more than two electrodes are used, and the depolarization and repolarization waves can be detected between any pair of electrodes. The output from each pair is known as a lead. Each lead looks at the heart from a different angle. Different types of electrocardiographs can be referred to by the number of leads that are recorded, for example, three-lead, five-lead or twelve-lead electrocardiographs. The standard electrocardiograph used to detect ischemia, injury, and infarction of the heart muscle is a twelve-lead electrocardiograph which uses ten electrodes (e.g., 4 limb electrodes and 6 chest electrodes). In a twelve-lead electrocardiograph, twelve different electrical signals are recorded at approximately the same time and typically recorded onto an 8½"×11" piece of special paper creating a one-off permanent record electrocardiograph at a single point in time. Three and five lead cardiograms tend to be displayed in continuous mode on the screen of an appropriate monitoring device, for example, during an operation or transportation in an ambulance, usually for the purpose of detecting disturbances of heart rhythm. There may or may not be any permanent record of a three or five lead electrocardiograph, depending on the equipment used.

SUMMARY

In accordance with an aspect of the present invention, an electrocardiograph system is provided. A set of electrodes is configured to detect a voltage differences between various pairs of locations on a body of a patient. A display is configured to visually represent digital signals derived from the plurality of detected voltage differences. A display interface is configured to format the digital signals for the display, such that the leads are grouped and displayed as a sequence of proper subsets or groups of the plurality of detected voltage differences. Each proper subset or lead group represents a specific anatomical structure of a heart of the patient.

In accordance with another aspect of the present invention, a non-transitory computer readable medium stores machine executable instructions for displaying leads from an electrocardiograph. The machine executable instructions being executable by an associated computer to perform a method that includes selecting a set of lead signals associated with one of the inferior, anterior, lateral, and posterior walls of the heart and displaying the selected set of lead signals. The steps of selecting a set of lead signals and displaying the selected set of lead signals are repeated until respective sets of leads associated with each of the inferior, anterior, lateral, and posterior walls of the heart have been displayed.

In accordance with yet another aspect of the present invention, a method is provided for performing an electrocardiograph on a patient. A set of electrodes is positioned on the patient. Voltage differences measured from the set of electrodes are processed to provide a plurality of lead signals representing activity of a heart of the patient. The lead signals are selectively displayed such that proper subsets of the plurality of lead signals, each representing an anatomical structure of the heart, are displayed in sequence to an operator.

DETAILED DESCRIPTION

Figure 1:
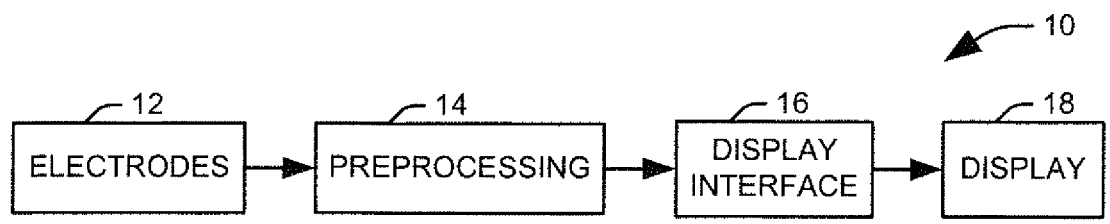
FIG. 1 illustrates an example of an electrocardiograph system in which the leads representing each of a plurality of anatomical structure are displayed in isolation.

Electrocardiographs are used to diagnose heart rhythm problems, such as atrial fibrillation, as well as myocardial ischemia or injury. Electrocardiographs are obtained acutely on any patient presenting with chest pain to a hospital emergency department for the purpose of detecting myocardial ischemia (e.g., lack of sufficient blood flow to a part of the heart) or injury (e.g., death of heart muscle to a part of the heart caused by a lack of blood flow to that part, such as a heart attack or myocardial infarction). Currently, most electrocardiographs in hospitals, particularly in emergency departments, are viewed on the hard copy paper that is produced by a twelve-lead electrocardiograph machine hooked up to the patient. One of the critical electrocardiograph tracing patterns that it is imperative to identify immediately is "ST Segment Elevation Myocardial Infarction (MI)." A myocardial infarction is a heart attack, that is, a blockage of blood flow in one of the coronary arteries that results in the death of the segment of heart muscle served by that artery. The reason for the time imperative in identifying this pattern is that the current standard of care mandates that the patient be taken immediately to the cardiac catheterization laboratory where a therapeutic angioplasty procedure can take place or, assuming no contraindications, be administered thrombolytic therapy to dissolve the clot that is blocking the coronary artery. The longer the time period between the onset of symptoms and the opening of the artery, the more heart muscle (myocardium) becomes dysfunctional. The physician reading the electrocardiograph is supposed to interpret it in a systematic manner, first assessing the rate, then the rhythm, then several key intervals (e.g., PR and QRS), then the shape and direction of the T wave and the shape and direction of the ST segment of the electrocardiograph. The ST segment is the segment of tracing that is located between the QRS complex and the T wave. The presence of ST segment elevation in specific leads, that is, a situation in which the ST segment is located above the "baseline" of the tracing for a given lead, means that there is an acute myocardial infarction occurring in the part of the heart that is represented by those leads. The location of the myocardial infarction is typically indicated as one of anterior (leads V1, V2, V3, and V4), lateral (leads 1, aVL, V5, and V6), inferior (leads 2, 3, aVF, and, in some applications, V1), and posterior (leads V1, V2, and, in some applications, V3).

There are few more hectic work environments than a hospital emergency department, and ST segment elevation myocardial infarctions are sometimes "missed" by the interpreting clinician. In other words, the treating clinician does not properly see or interpret the ST segment as being elevated, even though on closer scrutiny it is revealed to be elevated. A "missed MI" is one of the largest causes of malpractice settlements in emergency department care, because there is a direct correlation between time to treatment (e.g., angioplasty or thrombolytic therapy) and clinical outcome. Any delay in diagnosis and treatment can be translated into a worse clinical outcome for the patient. Therefore, it can be found for malpractice purposes that the harm that has accrued to the patient is a direct result of the violation of a standard of care by not identifying an ST segment elevation myocardial infarction.

The reasons that recognition of ST segment elevation is missed can vary, but several contributing factors can be identified. One reason is a rushed and non-systematic approach to electrocardiograph tracing interpretation, that is, a lack of mindfulness. The electrocardiograph is often thrust into the hands of a busy emergency department physician by a nurse or a technician who is looking to the physician to determine if the patient is having an ST segment myocardial infarction. The physician is typically already doing another task when given the electrocardiograph to read, and so is operating more in interrupt mode than in intentional mode. Further, the physician may perform more of a "gestalt" read with a single glance at the whole electrocardiograph, with the expectation that abnormal patterns of ST segment location and configuration will "pop out" as something abnormal. Most of the time this type of approach works, but subtle ST segment elevation, as often occurs in the inferior leads, is typically not seen or appreciated in a fleeting glance and a "missed MI" may result. Even if the physician "misses" only one out of twenty times, or five percent of the inferior wall myocardial infarctions presented to him or her, that is simply not a good enough "batting average", as each miss represents a potential one hundred percent negative outcome for that individual patient.

One of the most common types of ST segment elevation MI's missed by clinicians is an inferior wall myocardial infarctions which is reflected in the inferior electrocardiograph leads 2, 3, and F. The reason for this is that the inferior leads typically have lower overall voltage, reflected as a lower total height of the QRS complex on the electrocardiograph, than the anterior and lateral leads. Therefore the absolute amount of ST segment elevation, expressed in millimeters, is smaller than the amount of ST segment elevation that occurs in the anterior or lateral leads, but the amount of ST segment elevation relative to the total height of the QRS complex is no different, since the QRS complex height is also smaller in the inferior leads. It is easy to miss the subtle ST segment elevation that can occur in the inferior leads, especially when there is also a rushed and non-mindful encounter with the electrocardiograph tracing on the part of the physician.

To address these issues, a system is provided for displaying electrocardiograph data to a user, generally a physician, such that the data representing each of a plurality of anatomical structures are presented in isolation. In one implementation, the system sequentially presents to the physician a first display containing only the anterior leads, a second display containing only the lateral leads, a third display containing only the inferior leads, and a fourth display containing only the posterior leads, forcing the physician to focus on one part of the electrocardiograph at a time. Forcing the physician to view the electrocardiograph in multiple discrete parts, in addition to performing an initial global scan, is expected to create a more mindful approach to viewing the electrocardiograph. Specifically, the invention guides the physician through a sequence of steps that replicate what should be being done "virtually" in a systematic visual scan.

In one implementation, the system also preserves a spatial identity of each set of leads by displaying the leads in the spatial configuration with which the physician is used to viewing them. For example, the inferior leads 2, 3 and F are always located within a twelve-lead electrocardiograph, with lead two in a left hand part of the tracing and in the second row, lead three in a left hand part of the tracing and in the third row, and lead F in a second to left hand part of the tracing and in the third row. This provides a strong contextual cue to the physician as to which set of leads he or she is currently viewing. The leads that are not part of the group of leads being displayed are obscured. Experienced clinicians immediately recognize this L-shaped set of three leads in the lower left hand part of the electrocardiograph to be the leads representing the inferior wall of the heart. To further assist the review by the physician, each set of leads can be displayed with a degree of magnification (e.g., 200%) over their original size. This magnification makes detection of small absolute amounts of ST segment elevation much more visible and better able to be appreciated. The physician can configure the system to provide a desired degree of magnification within specified limits.

FIG. 1 illustrates an example of an electrocardiograph system 10 in which the leads representing each of a plurality of anatomical structure are displayed in isolation. The system 10 includes a set of electrodes 12 used to detect voltage differences between various pairs of locations on a body of a patient. It will be appreciated that the electrodes can be positioned such that the voltage differential between each pair of locations provides information as to the function and structure of at least a portion of a heart of the patient. In the illustrated implementation, a set of ten electrodes are used, and twelve electrical signals representing respective pairs of electrodes, referred to herein as "leads," are captured for analysis.

A decision that a physician must make in addition to whether an electrocardiograph shows an "abnormality" that may be indicative of myocardial ischemia or myocardial infarction. Additionally, when an abnormality is identified, the physician must determine whether that abnormality is known to be new compared to the findings on a previous electrocardiograph if available (e.g., from one hour, one day, one week, one month, or one year previous; typically the most recent previous electrocardiograph is selected for comparison). Further, it is important to determine whether that abnormality is found to have been present in identical form on a previously obtained electrocardiograph. This system provides a means by which the clinician can easily compare two electrographs by placing them side by side on the same screen. The electrocardiographs can be compared whole on whole, (e.g., 12 leads compared to 12 leads) compared wall by wall (e.g., a subset of the leads, usually 3 or 4), or compared lead by lead. The leads being compared are placed horizontally side by side so the eye can easily scan back and forth from left to right to left, which is easier and more natural to do than up to down to up, for the purpose of detecting differences.

An additional way to compare the same lead from a current and a previous electrocardiograph is to assess if they are different or the same (e.g., in terms of the configuration of their shape) is to highlight one of the leads and then drag it over the other lead in a superimposed manner. If the leads fit exactly, one over the other, especially the ST segment or the T wave, an assessment can be made that there is no significant interval change between the two leads. If the leads do not superimpose well and a difference in height or width of the ST segment or T wave of the tracing is detected, then the conclusion can be made that an interval change has occurred between the two electrocardiographs with all the clinical significance that portends. In one implementation, a portion of the of the two leads, such as a QRS wave, can be scaled to match one another, allowing for a normalized comparison of the two leads.

The signals from the electrodes 12 are provided to a preprocessing component 14 that conditions the signal for use by an associated display interface 16. For example, the preprocessing component can include one or more of analog or digital filters, amplifiers, analog-to-digital converters, and similar components for facilitating detection and processing of the lead signals. The display interface 16 translates and formats the lead signals for display at an associated display 18. For example, the display 18 can include a printer for providing a tracing of the electrocardiograph results on a physical medium, a video screen for displaying the results electronically, or any other appropriate means for providing the lead signals to a physician or technician in a human-comprehensible form. In one implementation, the display 18 includes both of these elements, with a paper electrocardiograph scanned into a viewing station comprising a computer with an attached scanner attached.

In accordance with an aspect of the present invention, the display interface 16 can be configured to selectively display the leads according to their relevance to a given anatomical structure. To this end, the leads can be divided into a plurality of sets and displayed in sequence, in which each set contains a proper subset of the plurality of leads representing an associated anatomical structure of the heart. It will be appreciated that, depending on the selection of represented anatomical structures, the sets may not collectively contain all of the recorded leads, and that a given lead may be a member of both sets. In another implementation, the anatomical structures are the inferior, lateral, anterior, and posterior walls of the heart. In this implementation, leads V1, V2, V3, and V4 belong to a first set representing the anterior wall, leads 1, aVL, V5, and V6 belong to a second set representing the lateral wall, leads V1, V2, and V3 belong to a third set representing the posterior wall, and leads V1, 2, 3, and aVF belong to a fourth set representing the inferior wall.

The purpose of sequencing the different subsets of lead tracings is to enable the clinician to focus his or her complete attention on just those leads which represent a specific wall of the heart (e.g., inferior, anterior, lateral, posterior) and not be distracted by having to view leads reflecting all walls simultaneously. Furthermore, each subset of leads that represents a specific wall of the heart is displayed spatially as a table in such a way that the configuration of the leads is identical to their position on the electrocardiograph twelve lead electrocardiograph and so the experienced clinician can identify which wall is being viewed by the spatial configuration of the leads.

In accordance with an aspect of the present invention, when the sets of leads are displayed in sequence, less than all of the leads are displayed to the user at a given point within the sequence. Accordingly, each of the displayed leads can be displayed in a magnified form, facilitating analysis of the leads. Further tools can be provided to an operator through an appropriate user interface to allow for changes to the magnification, position, and orientation of the leads within an associated display area. Accordingly, the system not only provides a reminder to the physician to carefully review the leads associated with each anatomical structure, but also provides tools to facilitate review.

In accordance with an aspect of the present invention, the display interface 16 can be configured to selectively display single leads either sequentially on automatic pacing, or nonsequentially to get a more detailed look at a full screen version of a single lead of both sets. In one implementation, the leads I, II, III, aVR, aVL, aVF, V1, V2, V3, V4, V5 and V6 can be viewed individually.

The tools provided to the user can also include the ability to display data representing multiple electrocardiographs; for example, by juxtapositioning or superimposing portions of multiple electrocardiographs. In one implementation, all or a portion of a given lead can be displayed alongside or superimposed over an exemplar, representing an electrocardiograph reading of a healthy heart. In another example, segments from different leads can be juxtaposed or overlapped to simplify comparison of the electrocardiograph data across leads. For example, the additional electrocardiograph data can represent prior data from the same patient, such that a treating physician can compare the data over a period of time.

FIGS. 2-11 are screenshots of an exemplary system in accordance with an aspect of the present invention. In the illustrated implementation, the system is a twelve lead electrocardiograph system in which the lead signals are digitized, either via dedicated hardware or via scanning of a paper copy, and provided to a user on a video screen. In this implementation, the anatomical structures are the inferior, lateral, anterior, and posterior walls of the heart, such that the leads are divided into four sets. To allow for a consistent discussion across screen shots, FIGS. 2-11 share a common numbering of display elements.

Figure 2:
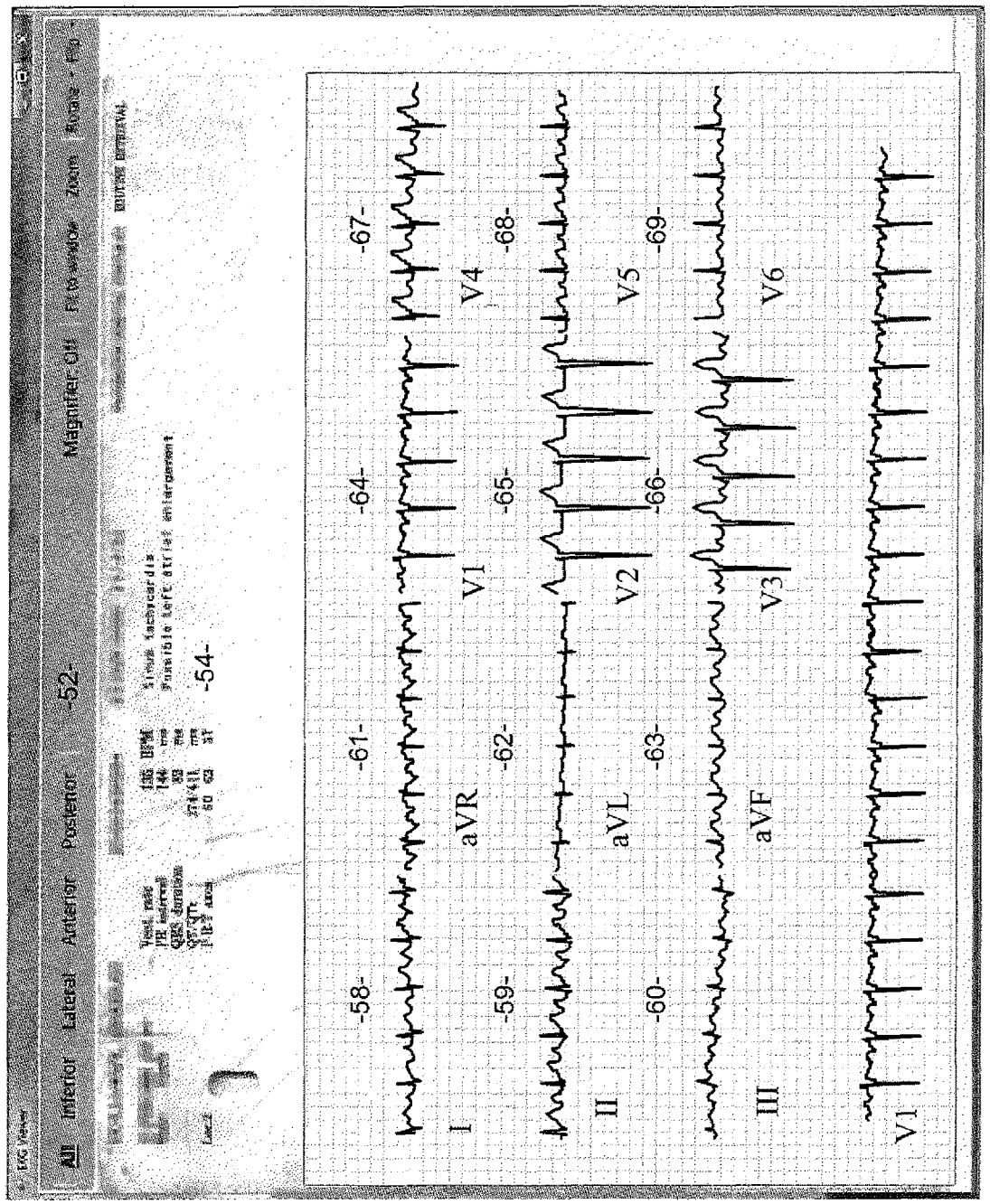
FIG. 2 is a screenshot of a display of the system in which all twelve leads are displayed.

FIG. 2 is a screenshot of a display of the system in which all twelve leads are displayed. The screenshot displays a menu bar 52 that can be interacted with by a user using an appropriate input device to access various features of the program. Features can include options for switching the set of leads currently displayed by the system, a zoom function, a magnifier for selectively enlarging a particular portion of the screen, a function to fit the image to an interface window, a rotate function, and a flip function. Patient information 54 is displayed below the menu bar, which can include identifying information, biometric parameters, and a preliminary diagnosis. Below the patient information, the twelve leads 58-69 are displayed. Each lead 58-69 is presented, by default, as an associated rectangular portion of the screen, although it will be appreciated that the size, position, and orientation of the leads can be altered by the user.

Figure 3:
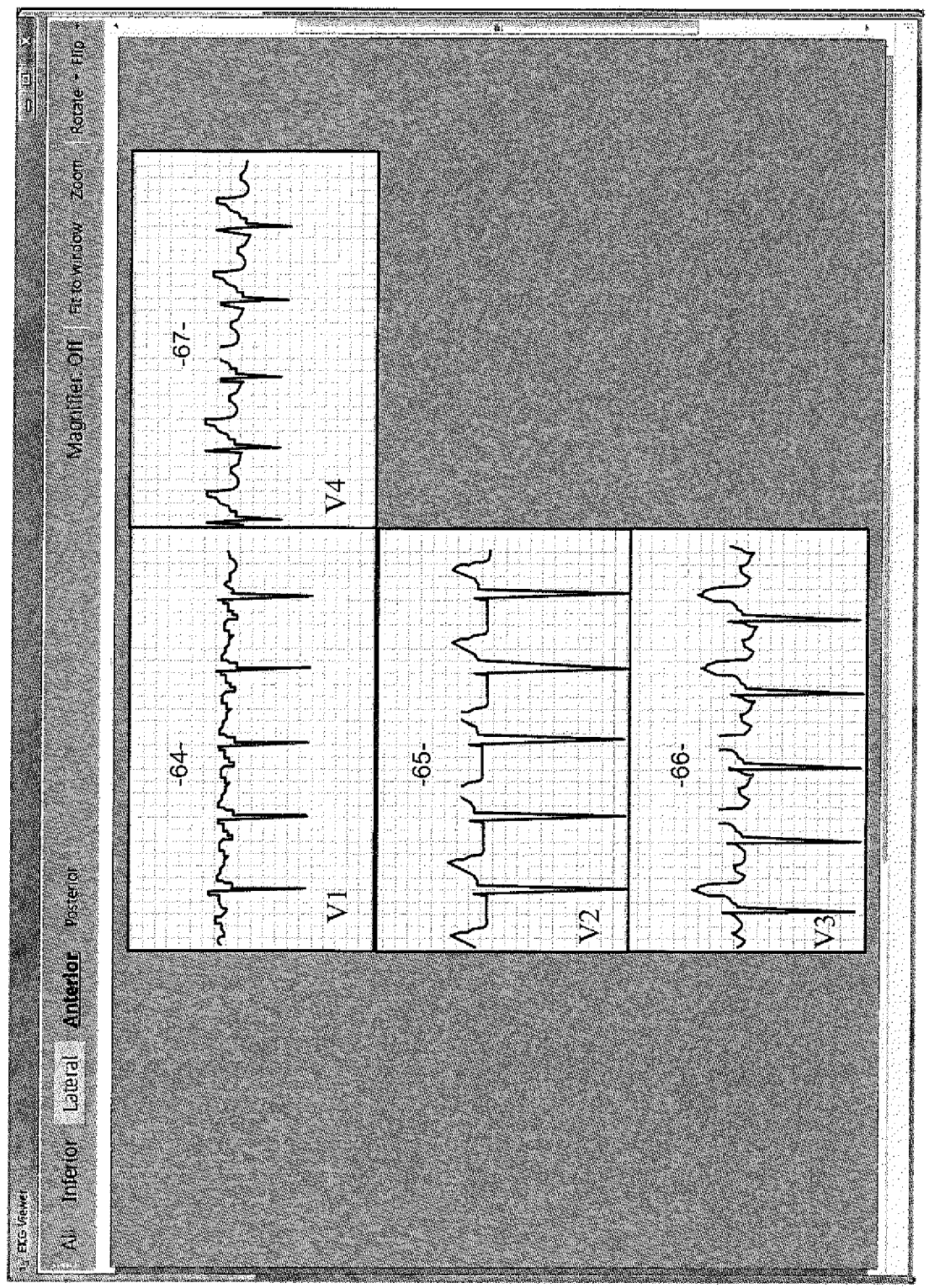
FIG. 3 is a screenshot illustrating the display of the system when only the set of leads representing the anterior wall of the heart are displayed.
Figure 4:
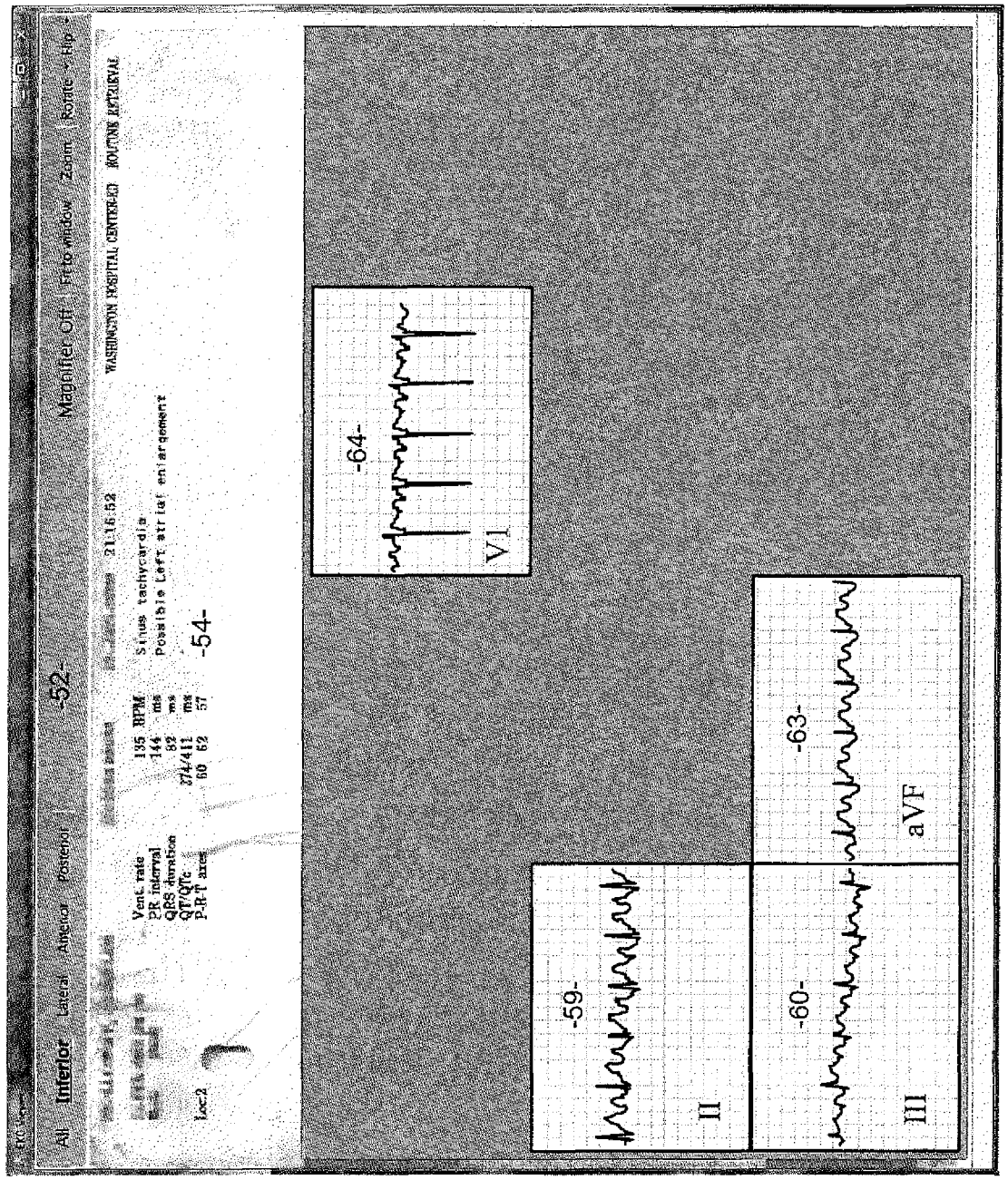
FIG. 4 is a screenshot illustrating the display of the system when only the set of leads representing the inferior wall of the heart are displayed.
Figure 5:
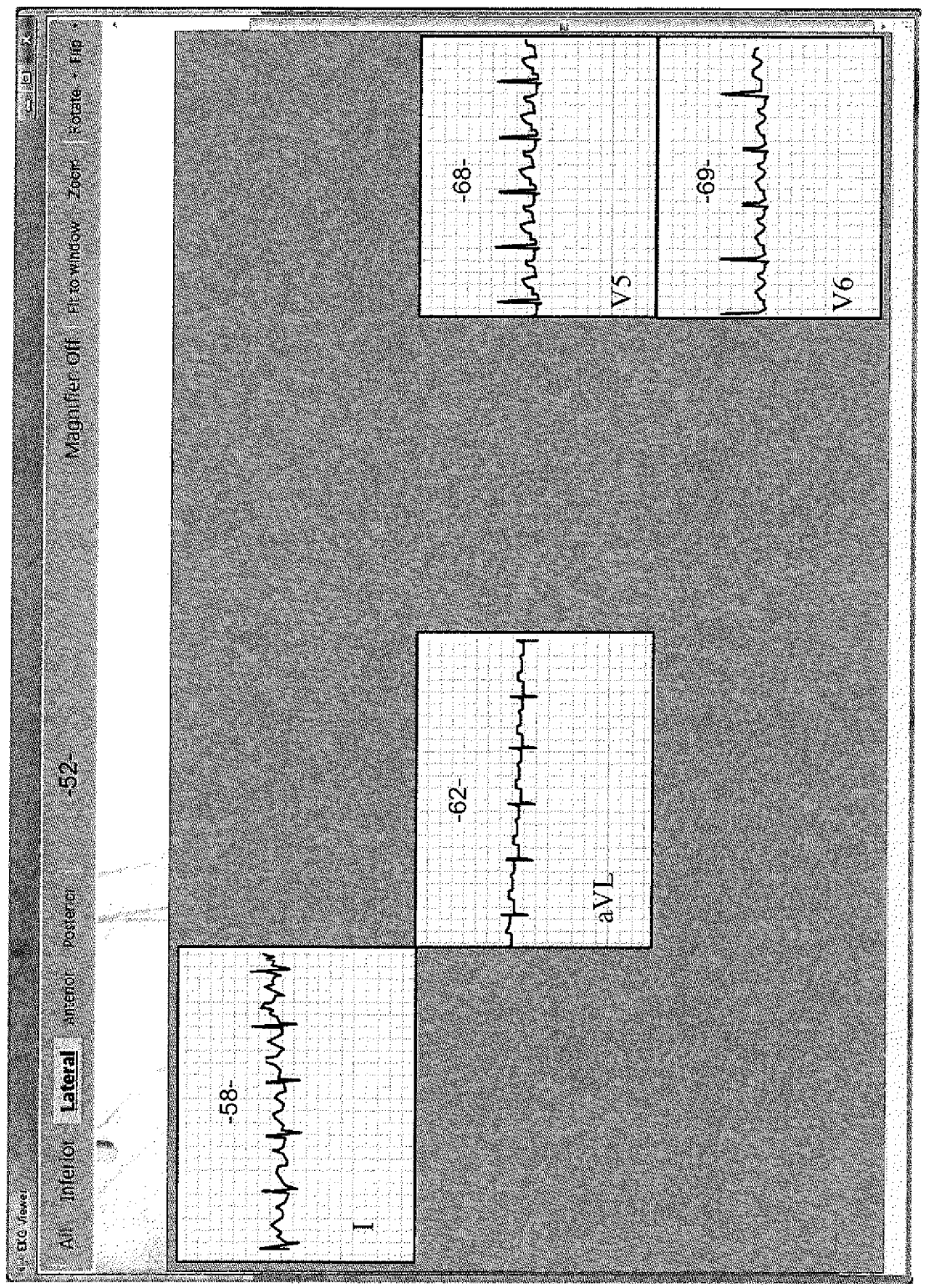
FIG. 5 is a screenshot illustrating the display of the system when only the set of leads representing the lateral wall of the heart are displayed.
Figure 6:
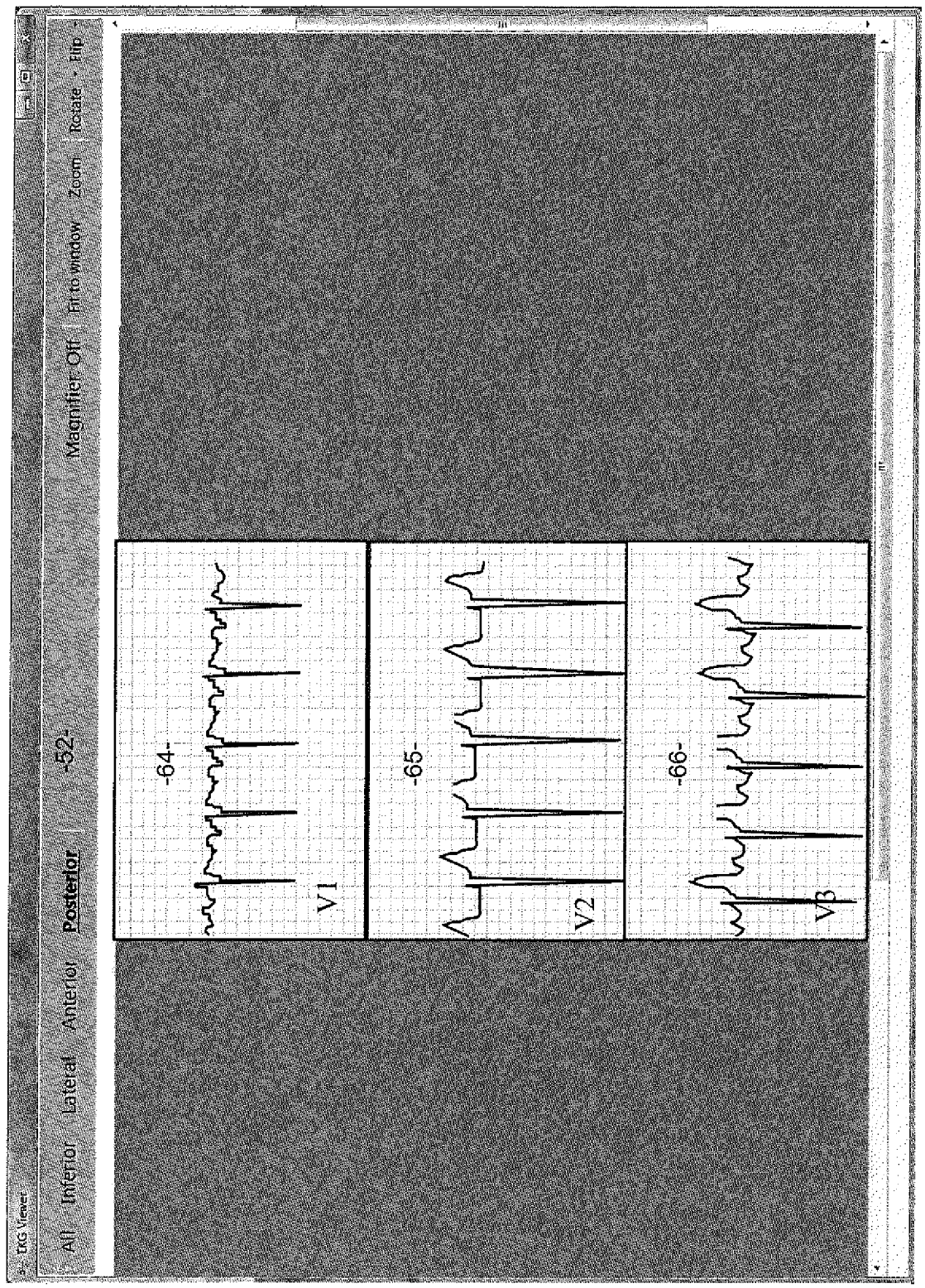
FIG. 6 is a screenshot illustrating the display of the system when only the set of leads representing the posterior wall of the heart are displayed.

FIG. 3 is a screenshot illustrating the display of the system when only the set of leads representing the anterior wall of the heart are displayed, specifically lead V1 64, lead V2 65, lead V3 66, and lead V4 67. It will be noted that in this arrangement, the patient information 54 has been hidden to increase the space available for viewing the leads. FIG. 4 is a screenshot illustrating the display of the system when only the set of leads representing the inferior wall of the heart are displayed, specifically lead II 59, lead III 60, lead aVF 63, and lead V1 64. FIG. 5 is a screenshot illustrating the display of the system when only the set of leads representing the lateral wall of the heart are displayed, specifically lead I 58, lead aVL 62, lead V5 68, and lead V6 69. FIG. 6 is a screenshot illustrating the display of the system when only the set of leads representing the posterior wall of the heart are displayed, specifically lead V1 64, lead V2 65, and lead V3 66. It will be appreciated that the screens illustrated in FIGS. 3-6 could be displayed to a user in a predetermined sequence to ensure that the leads associated with each wall of the heart have been reviewed. Further, it will be appreciated that the screens illustrated in FIGS. 3-6 include one possible arrangement of leads for each heart wall, and that other arrangements are possible, for example, excluding the V1 lead from the inferior wall set and the V3 lead from the posterior wall set.

Figure 7:
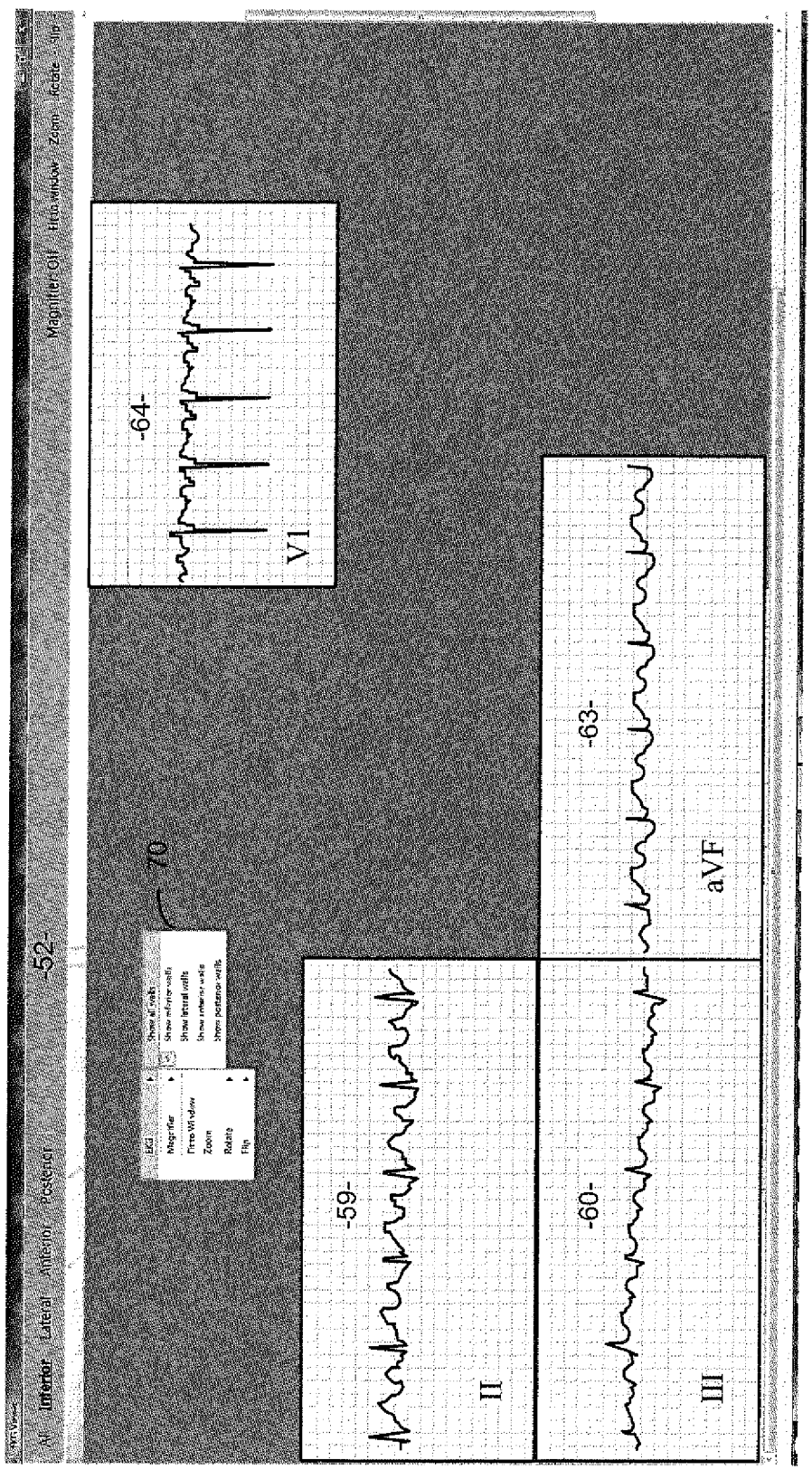
FIG. 7 is a screenshot illustrating a menu for switching among sets of leads for display.
Figure 8:
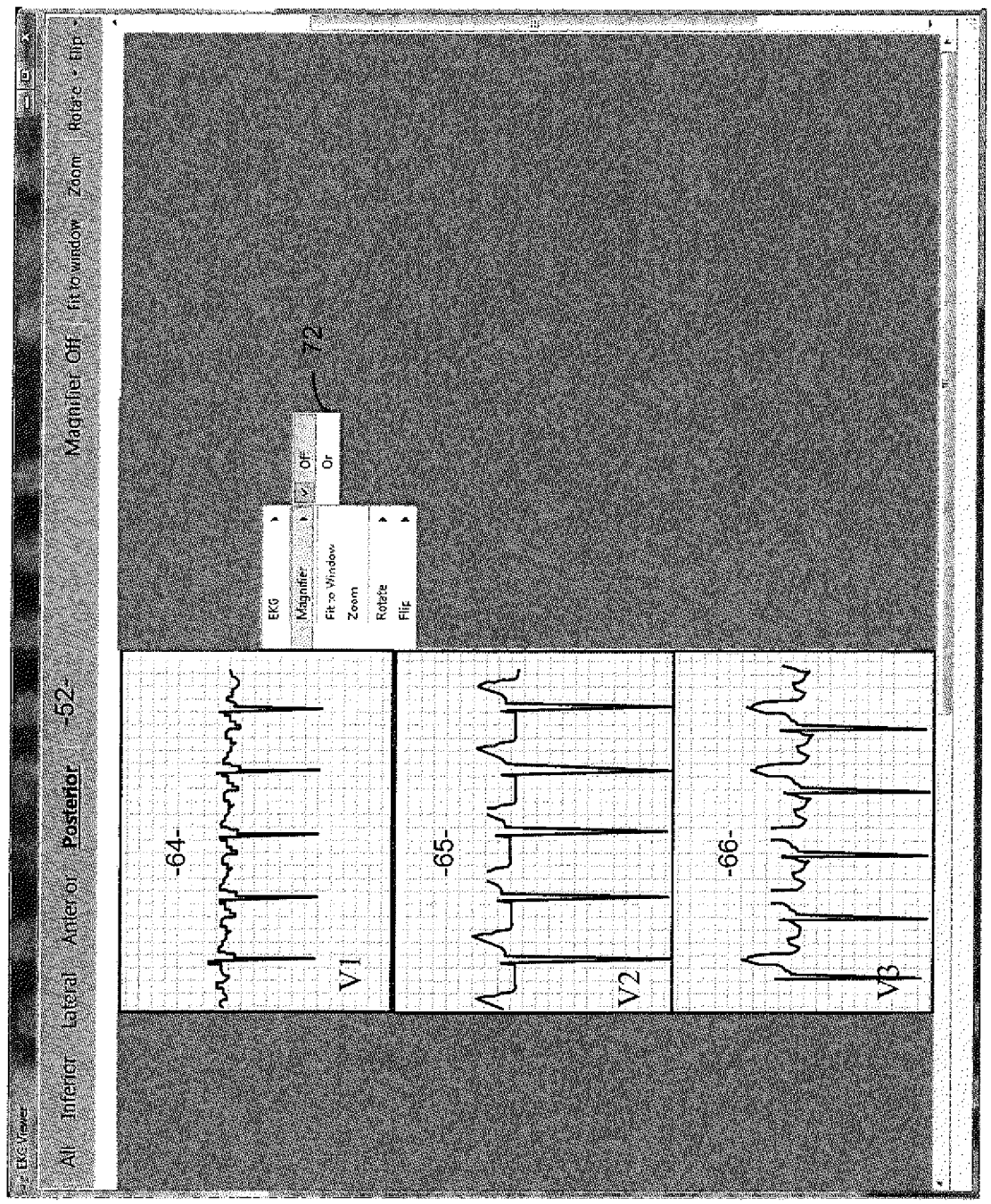
FIG. 8 is a screenshot illustrating a menu for selecting a magnifier function of the system.
Figure 9:
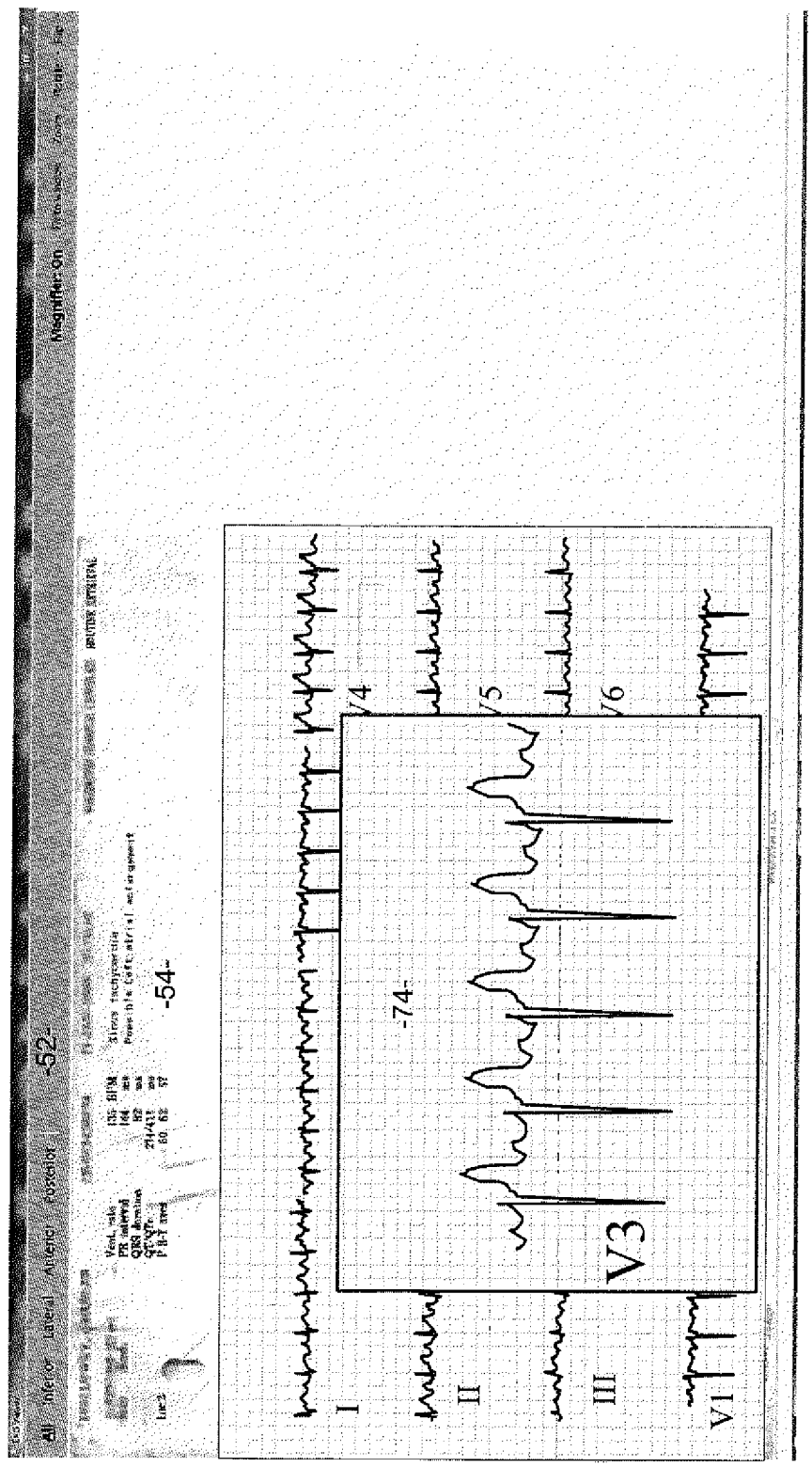
FIG. 9 is a screenshot illustrating a magnifier function of the system.

FIGS. 7-11 illustrate various tools for interacting with the displayed leads. In FIG. 7, the system is displaying the leads 59, 60, 63, and 64 associated with the inferior wall. A first menu 70 can be opened by the user with an appropriate input device, for example, a computer mouse or stylus, to allow the user to quickly change among the sets of leads representing the various heart walls. In FIG. 8, the system is displaying the leads 64-66 associated with the posterior wall. A second menu 72 can be opened by a user with the input device to allow a magnification function of the system to be activated. FIG. 9 shows the system with a portion 74 of lead V3 magnified. It will be appreciated that the position and degree of this magnification is controllable by the user to facilitate review of the electrocardiograph leads. In one implementation, the user can shift a given lead or small group of leads to a full screen view. The viewing of full screen leads can be done manually, stepping sequentially or non-sequentially through the leads, or the user can step through the walls and leads automatically. The user or an administrator has the capability to set the timing for how long an individual wall or lead stays on the screen until it is replaced by the next wall or lead in sequence.

Figure 10:
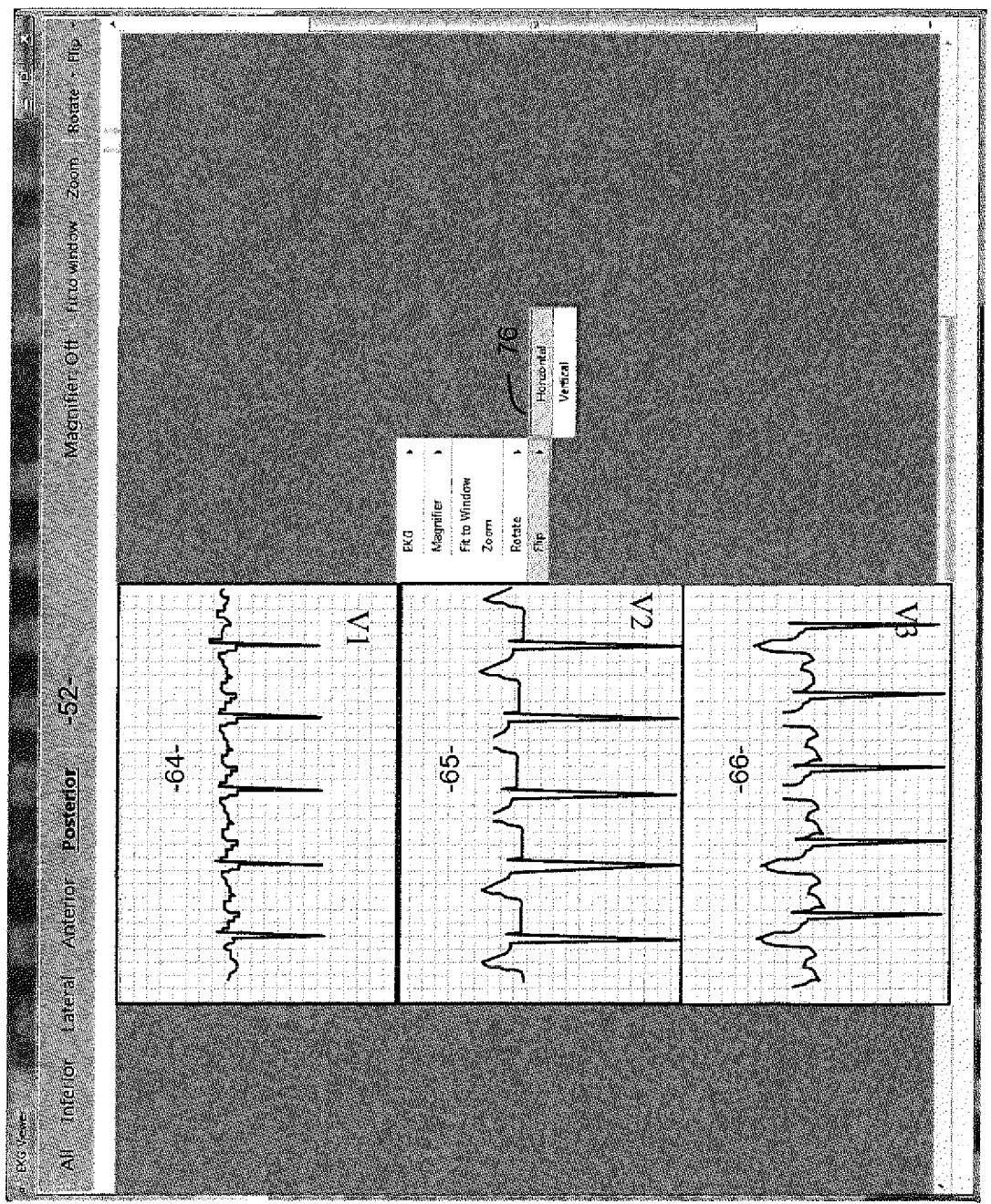
FIG. 10 is a screenshot illustrating a flip function of the system.
Figure 11:
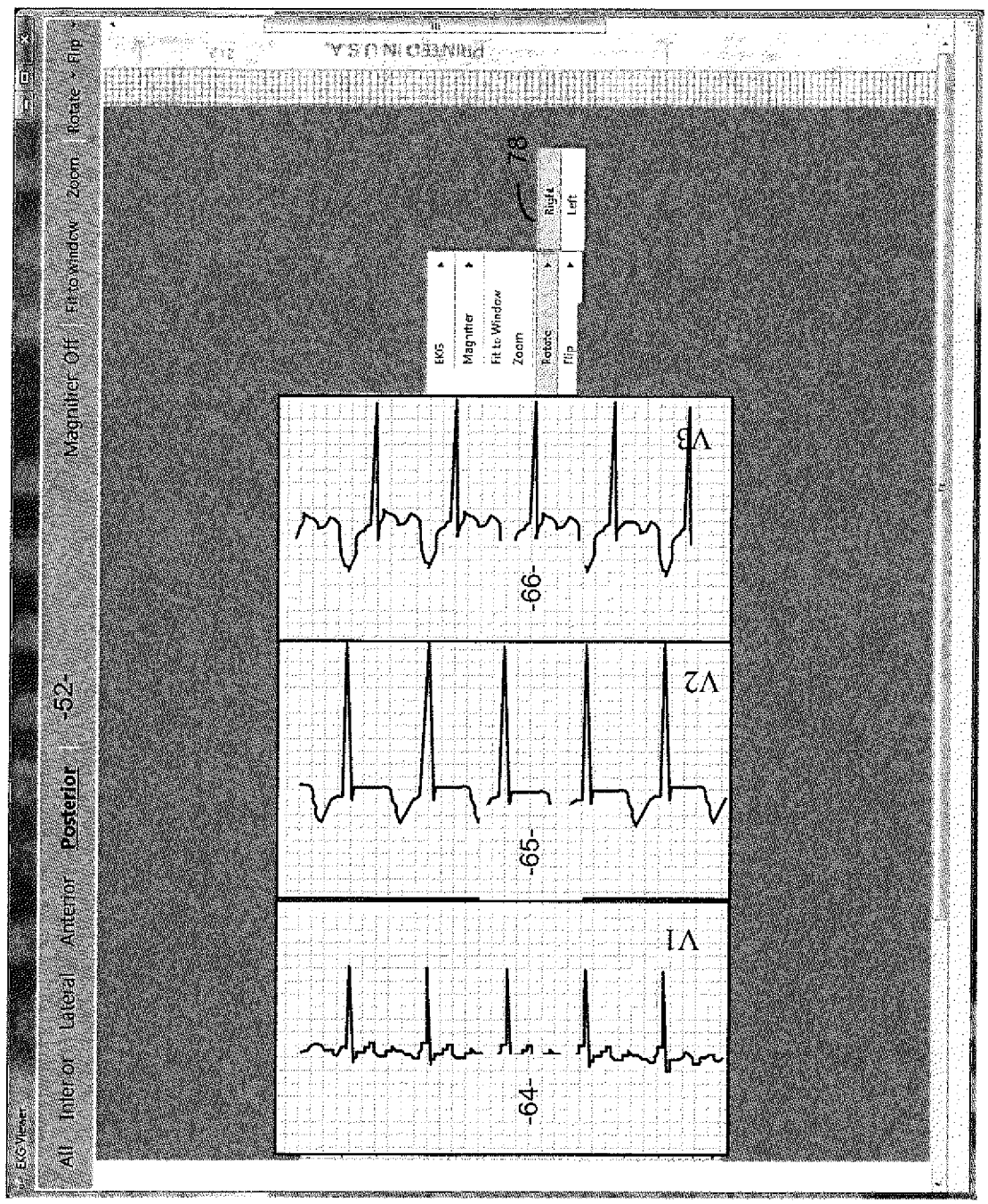
FIG. 11 is a screenshot illustrating a rotate function of the system.

In FIG. 10, the system is displaying the leads 64-66 associated with the posterior wall, but they have been reversed using a flip function of the system. The flip function can be accessed by a user with the input device via a third menu 76 to flip one or more selected leads, that is, transform the lead such that an order of the pixels in each row is reversed. In FIG. 11, the system is displaying the leads 64-66 associated with the posterior wall, but they have been rotated ninety degrees counterclockwise by a rotation function of the system. The rotation function can be accessed by a user with the input device via a fourth menu 78 to rotate one or more selected leads by a desired angle.

Figure 12:
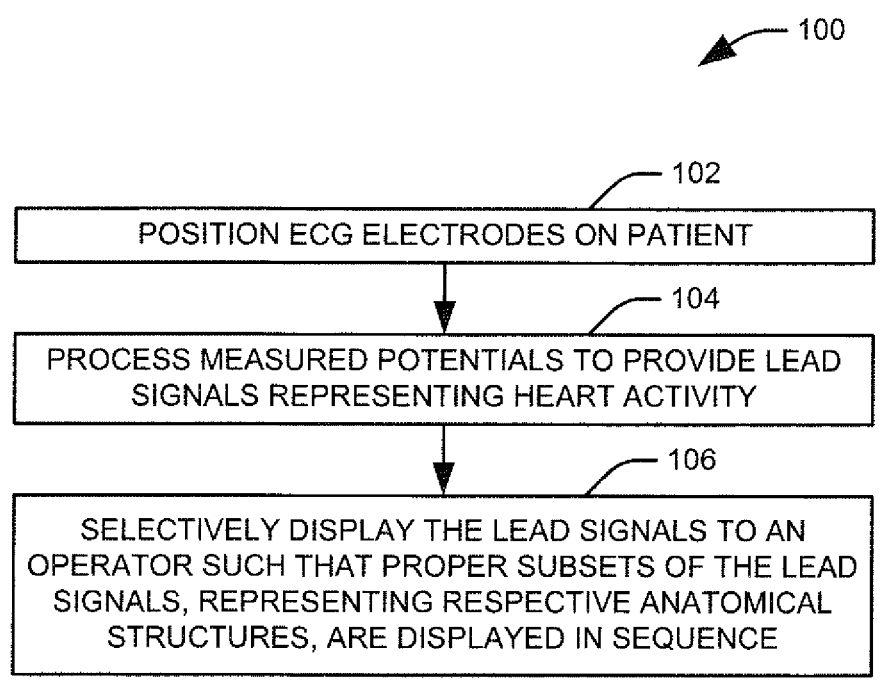
FIG. 12 illustrates one example of a method for performing an electrocardiograph on a patient in accordance with an aspect of the present invention.

FIG. 12 illustrates one example of a method 100 for performing an electrocardiograph on a patient in accordance with an aspect of the present invention. At 102, a set of electrodes is positioned on the patient. It will be appreciated that the number and placement of the electrodes will vary with the application, but in a twelve-lead system, ten electrodes can be used, with six placed on the chest, and one on each limb. At 104, voltage differences measured from the set of electrodes are processed to provide a plurality of lead signals representing activity of a heart of the patient. For example, the signals can be filtered, amplified, and converted to a digital signal to facilitate analysis ad display of the lead signals At 106, the lead signals are selectively displayed such that proper subsets of the plurality of lead signals, each representing an anatomical structure of the heart, are displayed in sequence to an operator. Effectively, rather than overwhelming the operator with information, the system displays the lead signals in manageable units, with each unit representing an anatomical structure of the heart of interest in evaluating the lead signals. In one example, each proper subset contains the leads signals representing an associated one of the inferior, anterior, posterior, and lateral walls of the heart. Accordingly, the operator is encouraged to examine the lead signals for each heart wall separately, allowing for a thorough examination of the electrocardiograph results.

Figure 13:
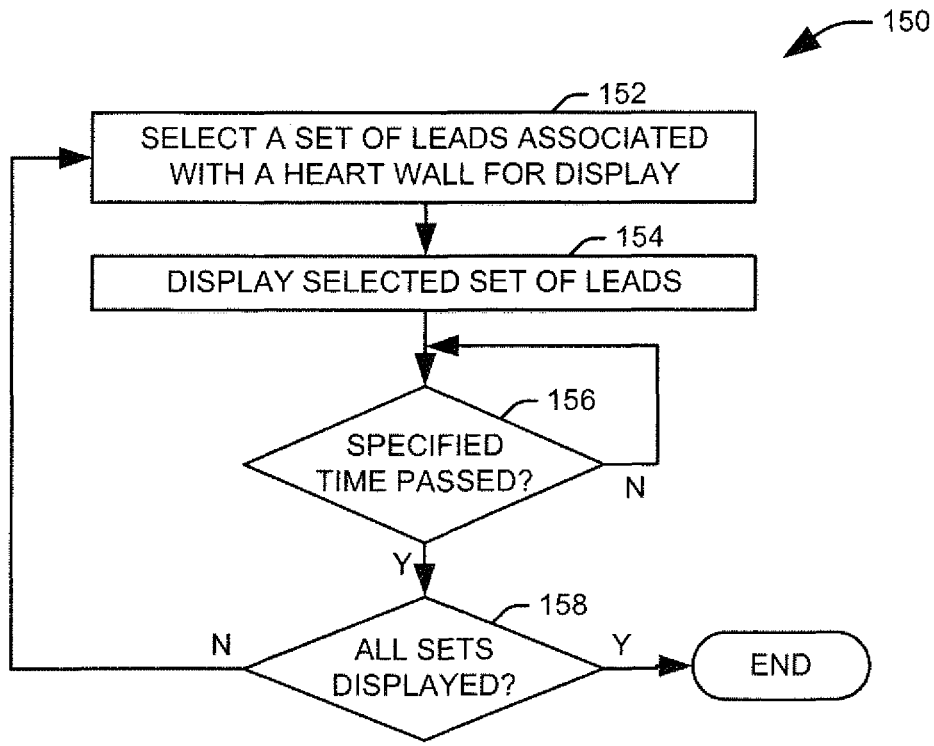
FIG. 13 illustrates a first method for displaying electrocardiograph results of a patient.

FIG. 13 illustrates a first method 150 for displaying electrocardiograph results to a patient. In the illustrated method 150, the lead signals are divided into sets representing, respectively, the inferior, anterior, posterior, and lateral walls of the heart. At 152, a next set of lead signals representing one of the walls of the heart are selected. It will be appreciated that an order for displaying the heart walls can be arbitrary or selected by a supervising physician to ensure that the heart walls most likely to exhibit abnormalities are displayed at the beginning of the sequence. At 154, the selected set of lead signals is displayed.

At 156, it is determined if a predetermined amount of time has passed. For example, a default time for reviewing each set of lead signals can be selected by a supervising physician. In one implementation, different time periods can be selected for each set of lead signals. Until the predetermined amount of time has passed (N), the method remains at 156 and the selected set of lead signals remains on the display. Once the predetermined amount of time has passed (Y), the method advances to 158, where it is determined if the lead signals associated with all four heart walls have been displayed. If not (N), the method returns to 152 to select a next set of lead signals. If the lead signals associated with all four walls of the heart have been displayed (Y), the method ends.

Figure 14:
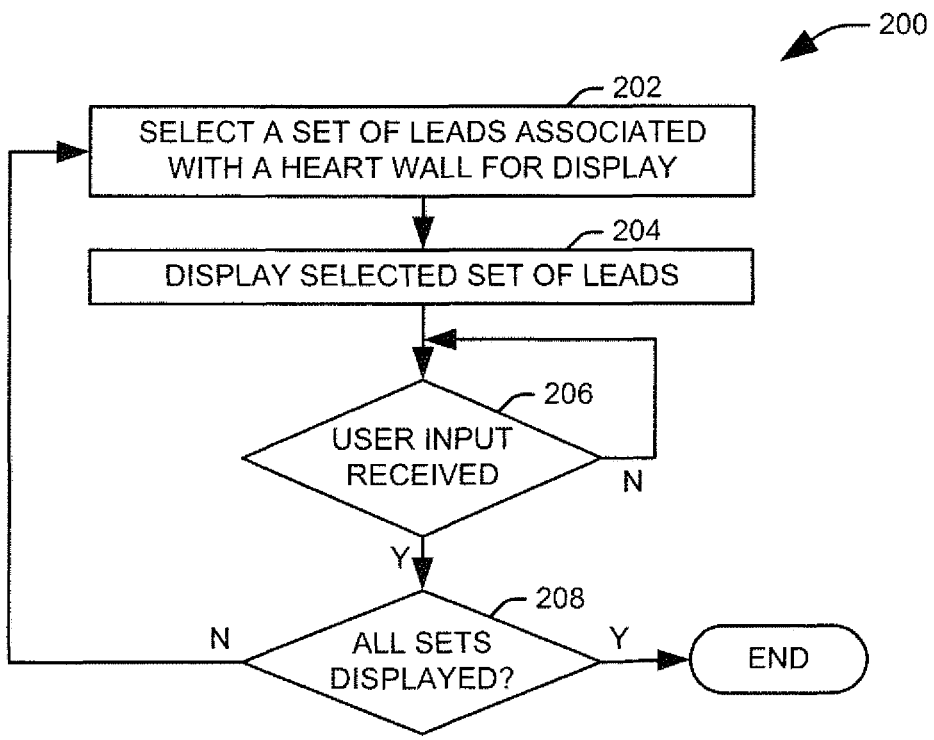
FIG. 14 illustrates a second method for displaying electrocardiograph results of a patient.

FIG. 14 illustrates a second method 250 for displaying electrocardiograph results to a patient. As in the method illustrated in FIG. 13, in the illustrated method 200 the lead signals are divided into sets representing, respectively, the inferior, anterior, posterior, and lateral walls of the heart. At 202, a next set of lead signals representing one of the walls of the heart is selected. As described previously, an order for displaying the heart walls can be arbitrary or selected by a supervising physician. At 204, the selected set of lead signals is displayed. At 206, it is determined if an input from the user has been received. If no input has been received (N), the method remains at 206, and the selected set of lead signals remains on the display until an input is received. Once an input has been received (Y), the method advances to 208, where it is determined if the sets of leads signals associated with all four heart walls have been displayed. If not (N), the method returns to 202 to select a next set of lead signals. If the lead signals associated with all four walls of the heart have been displayed (Y), the method ends.

Figure 15:
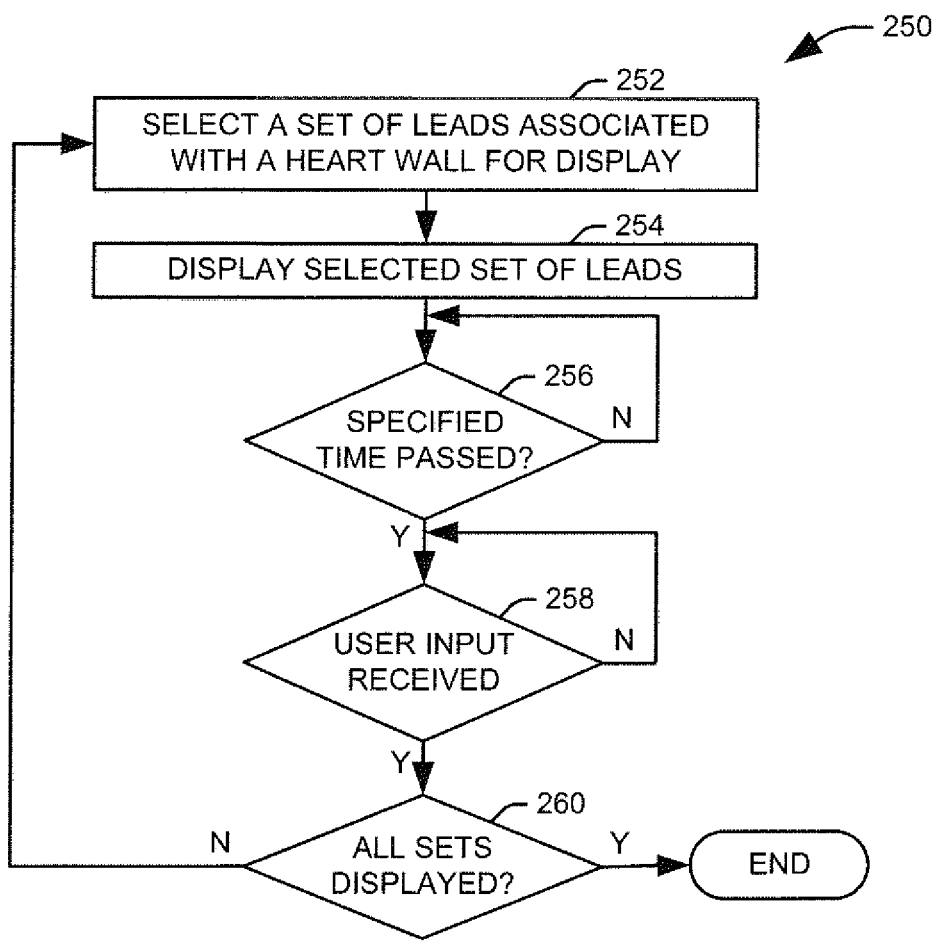
FIG. 15 illustrates a third method for displaying electrocardiograph results of a patient.

FIG. 15 illustrates a third method 250 for displaying electrocardiograph results to a patient. As in the methods illustrated in FIGS. 13 and 14, in the illustrated method 250 the lead signals are divided into sets representing, respectively, the inferior, anterior, posterior, and lateral walls of the heart. At 252, a next set of lead signals representing one of the walls of heart are selected. As described previously, an order for displaying the heart walls can be arbitrary or selected by a supervising physician. At 254, the selected set of lead signals is displayed. At 256, it is determined if a predetermined amount of time has passed. For example, a default time for reviewing each set of lead signals can be selected by a supervising physician. In one implementation, different time periods can be selected for each set of lead signals. Until the predetermined amount of time has passed (N), the method remains at 256 and the selected set of lead signals remains on the display.

Once the predetermined amount of time has passed (Y), the method advances to 258, where it is determined if an input from the user has been received during the predetermined amount of time. If no input has been received (N), the method remains at 258, and the selected set of lead signals remains on the display until an input is received. If an input has been received (Y), either during the predetermined amount of time at 256 or subsequently, the method advances to 260, where it is determined if the sets of leads signals associated with all four heart walls have been displayed. If not (N), the method returns to 252 to select a next set of lead signals. If the lead signals associated with all four walls of the heart have been displayed (Y), the method ends.

Clinicians utilize electrocardiographs to identify abnormalities that serve as indicators of a potential heart condition. Often indicators are subtle or easily overlooked due to environmental distractions inherent to a clinical setting, or due to time constraints. Tools that aid in identifying abnormalities and highlighting areas of concern and then bring them to the attention of the responsible clinician have a potentially lifesaving impact.

The inventors have determined that information pertaining to the nature of the abnormality can be critical to the type of treatment required. For example, whether that abnormality is known to be new compared to the findings on a previous electrocardiograph, or whether that abnormality is found to have been present in identical form on a previously obtained electrocardiograph, can be instructive to a treating clinician. The system described herein provides a means by which the clinician can easily compare two electrocardiographs by placing them side by side on the same screen. The electrocardiographs can be compared whole on whole, compared wall by wall, or compared lead by lead.

This approach is particularly useful for patients with a history of medical issues, where multiple electrocardiographs may be acquired for a specific patient over time. As described below, a variety of tools make a more detailed comparison of two or more electrocardiographs available to a clinician. Analytical tools implemented by the processing components can provide a computer based data point comparison. Also, multiple display configurations are considered that facilitate visual comparison by the clinician.

Figure 16:
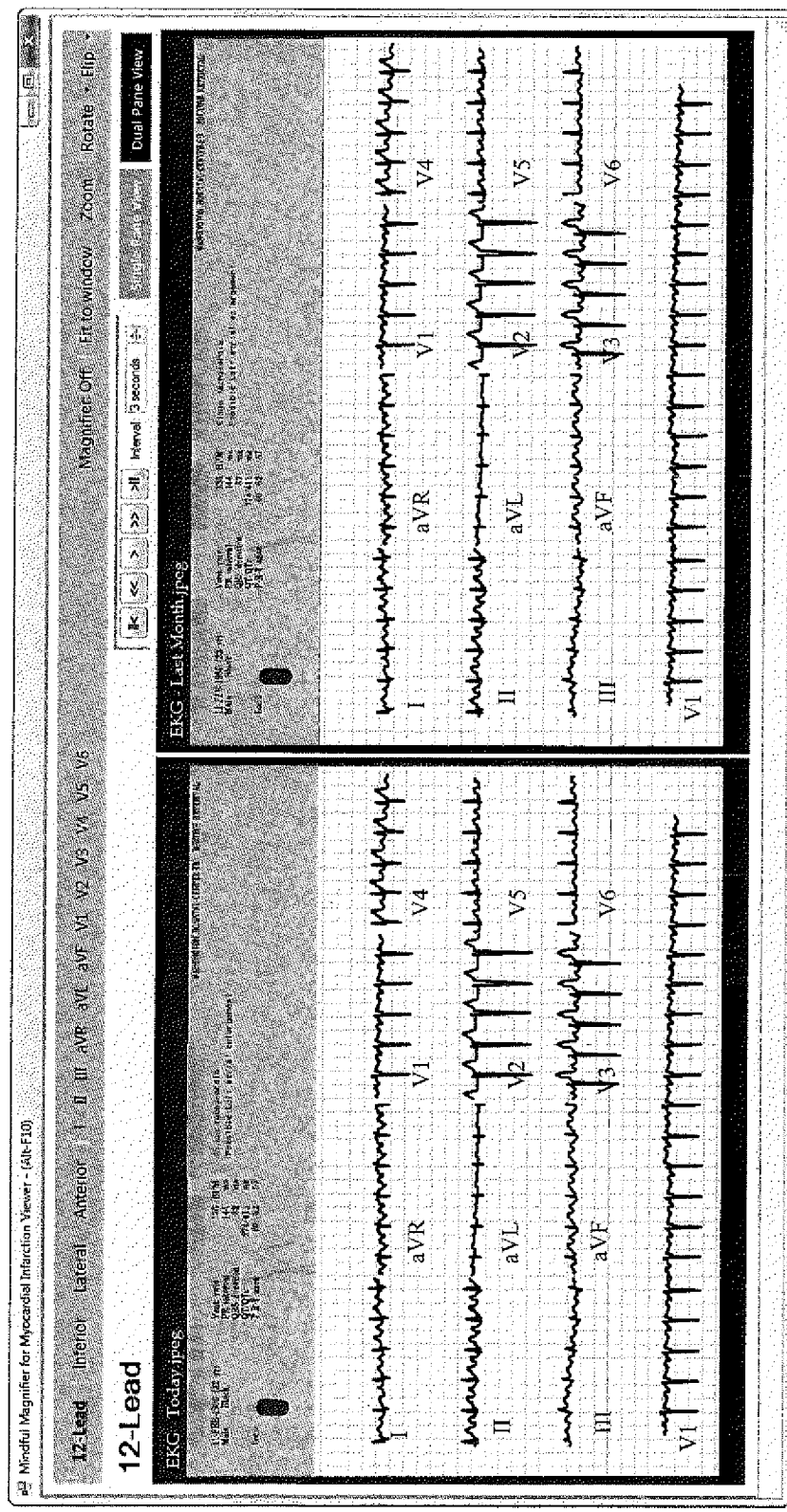
FIG. 16 is a screenshot illustrating the display of the system when two 12 lead electrocardiographs are displayed in a dual pane view.

For example, the clinician may select one or more leads of interest for display, the two images representing a current and a previous electrocardiograph, as shown in FIG. 16. The selected leads can also be isolated and presented for both the current and previous electrocardiograph, as shown in FIGS. 17 to 28. The selected leads of the two electrocardiographs can then be displayed side by side for ease of comparison. As described above, only the leads associated with the particular selection are displayed.

Figure 17:
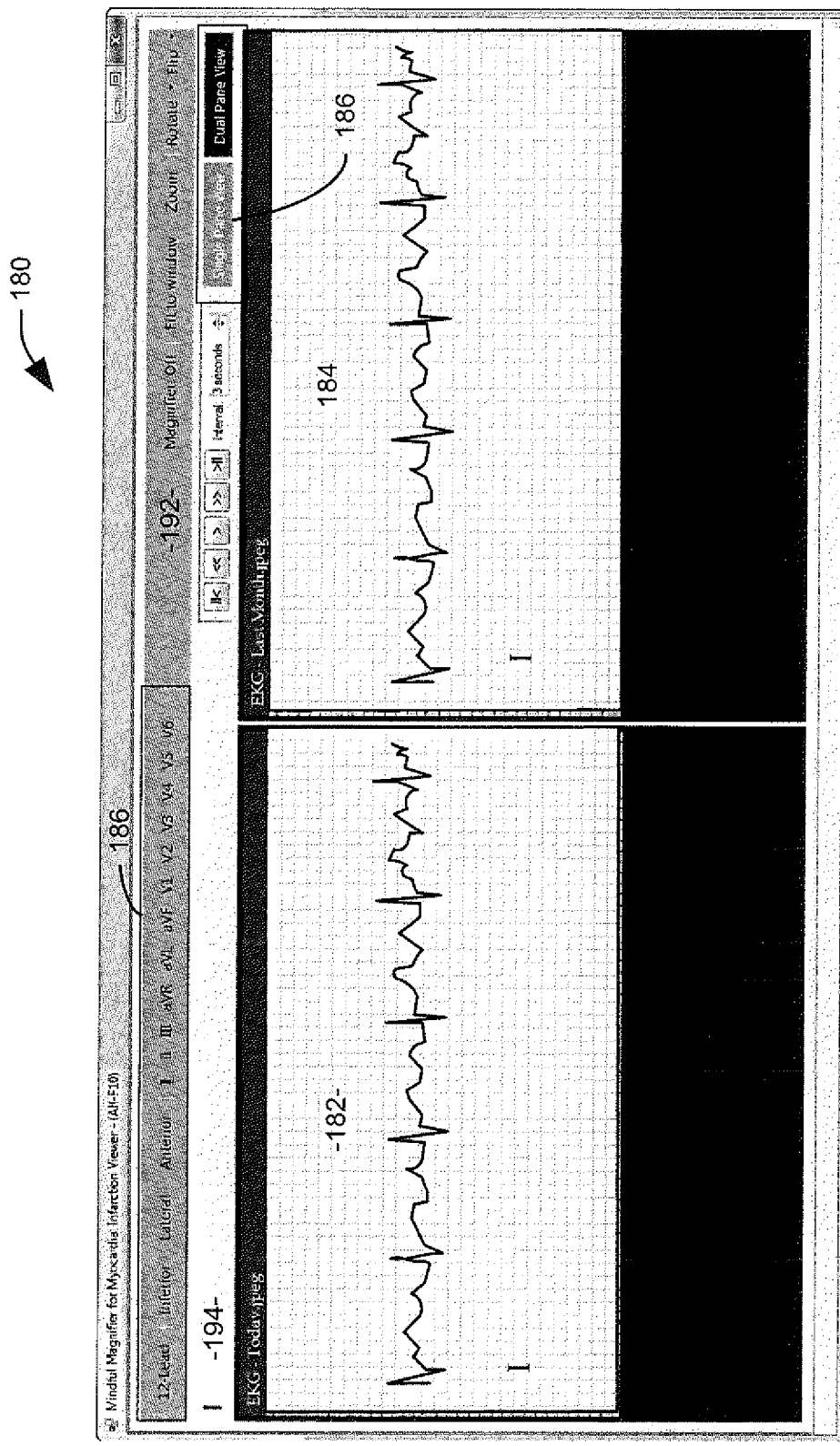
FIG. 17 is a screenshot illustrating the display of the system when two I lead electrocardiographs are displayed in a dual pane view.
Figure 18:
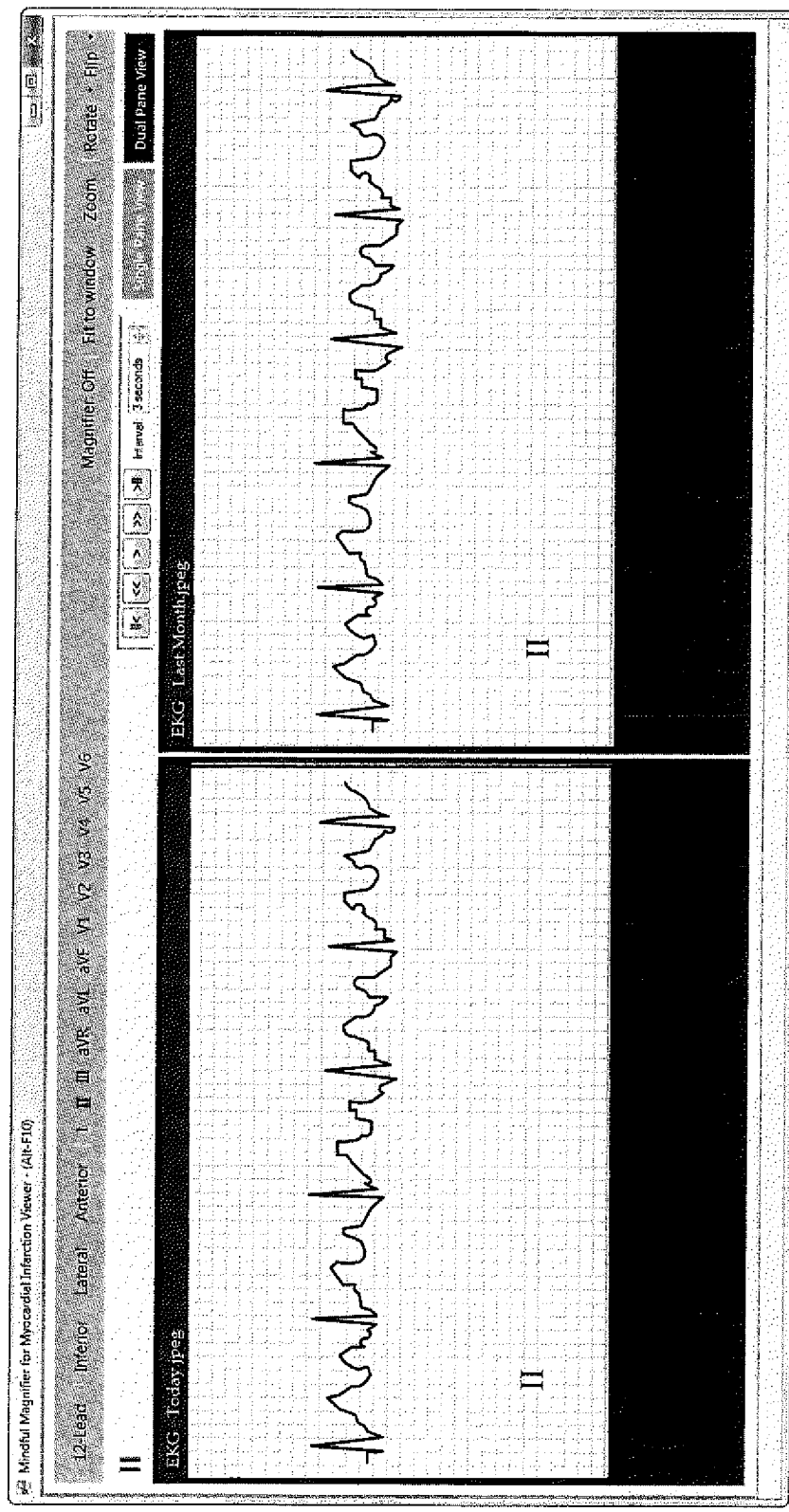
FIG. 18 is a screenshot illustrating the display of the system when two II lead electrocardiographs are displayed in a dual pane view.
Figure 19:
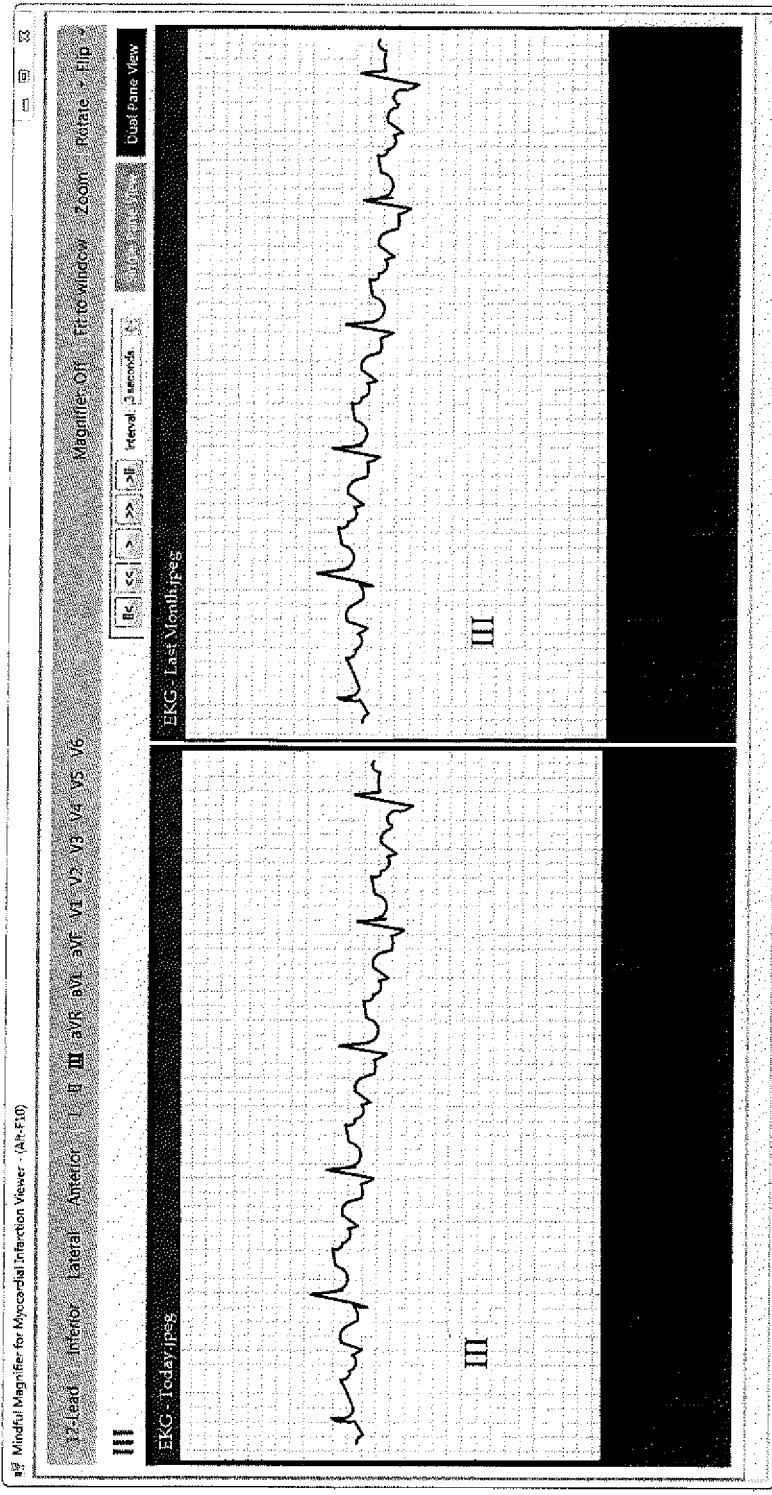
FIG. 19 is a screenshot illustrating the display of the system when two III lead electrocardiographs are displayed in a dual pane view.
Figure 20:
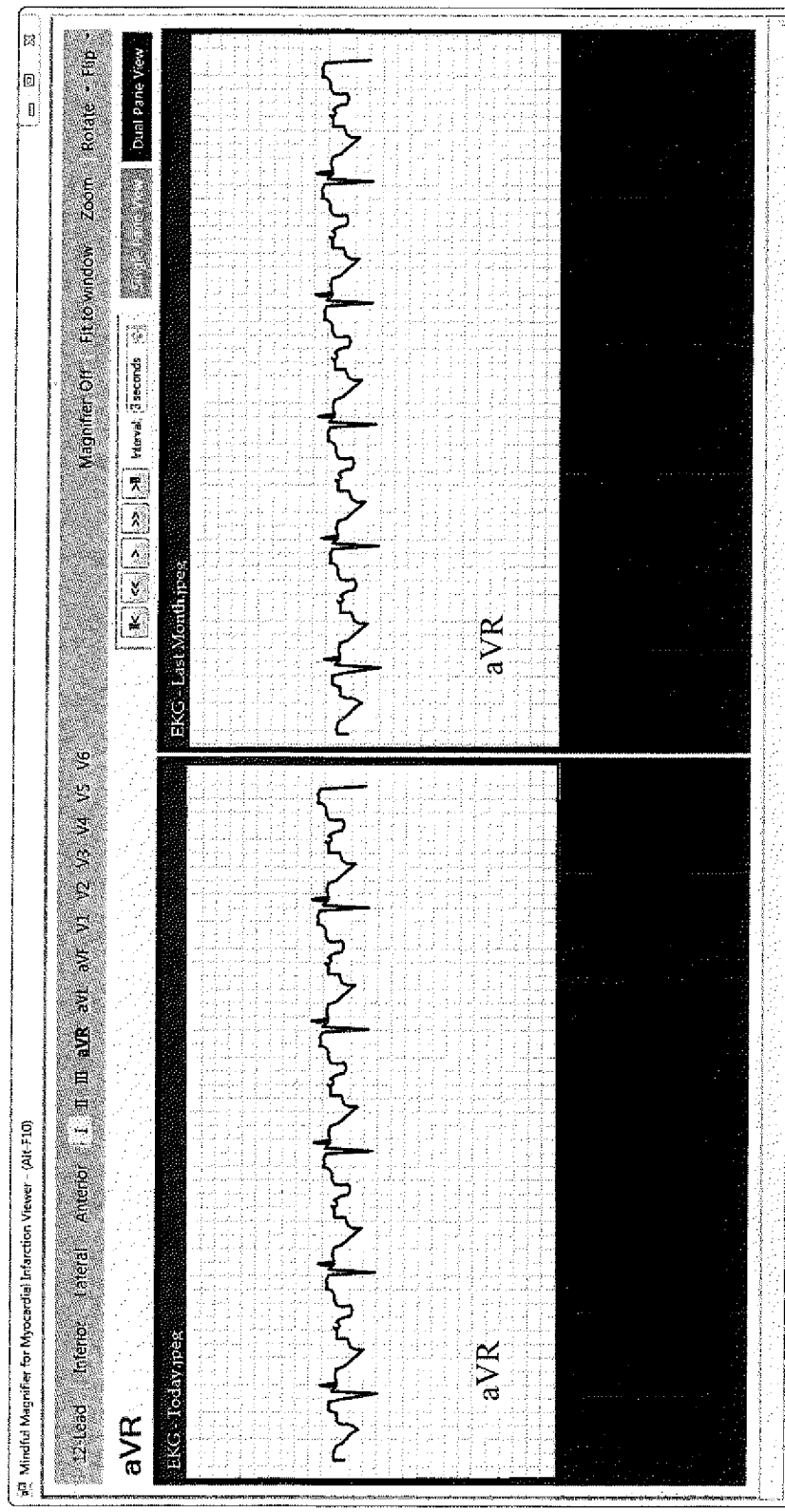
FIG. 20 is a screenshot illustrating the display of the system when two aVR lead electrocardiographs are displayed in a dual pane view.
Figure 21:
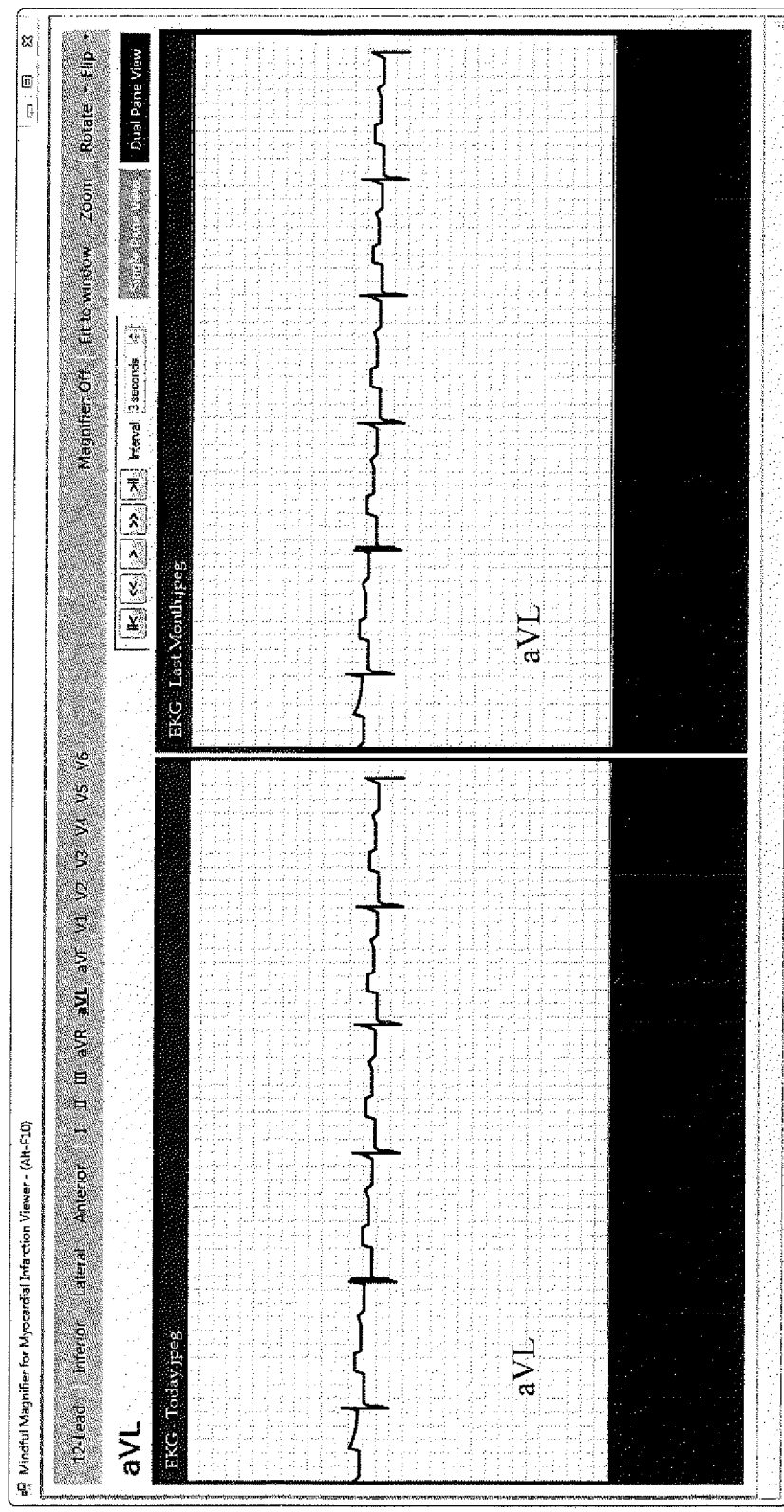
FIG. 21 is a screenshot illustrating the display of the system when two aVL lead electrocardiographs are displayed in a dual pane view.
Figure 22:
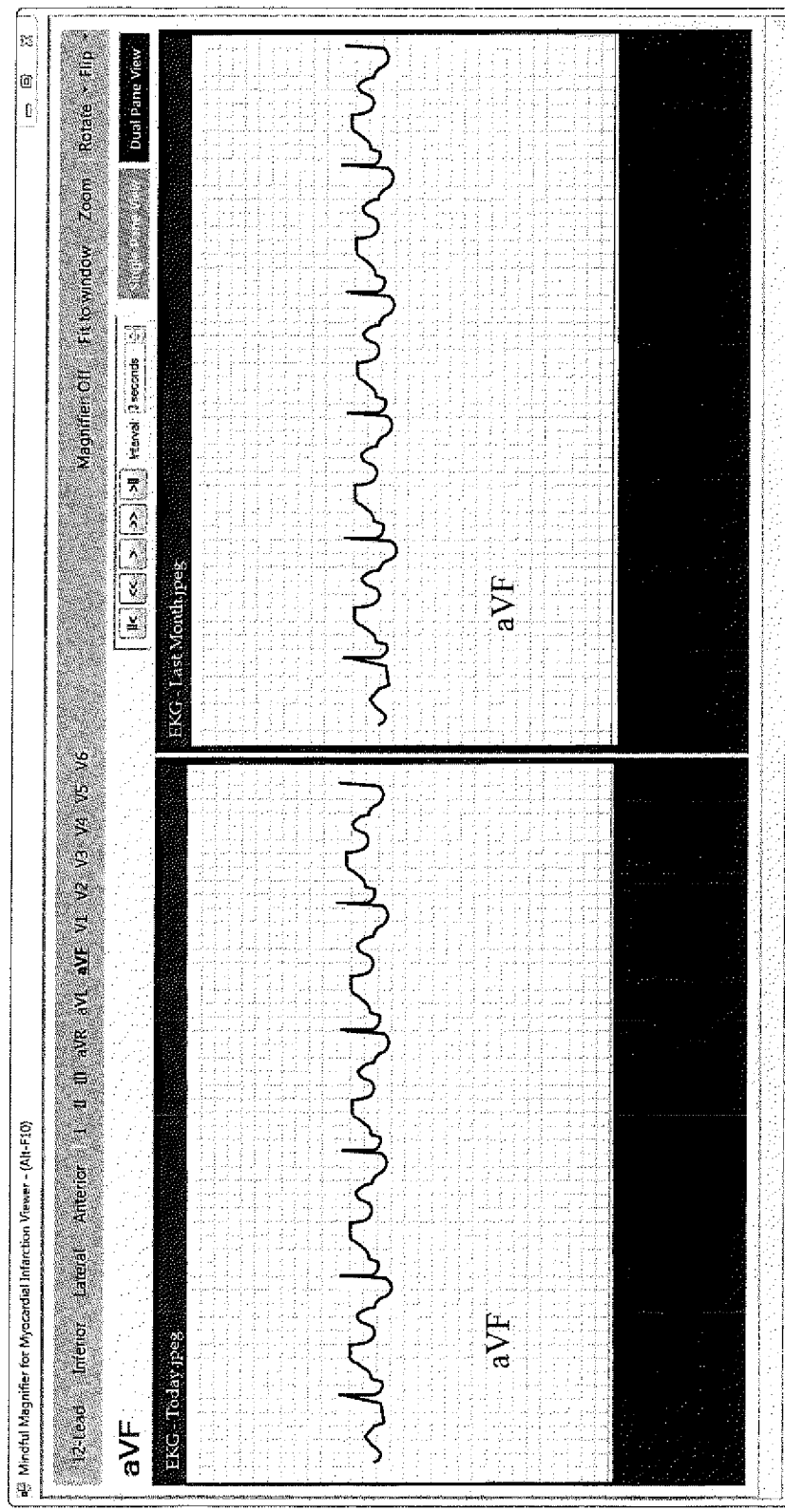
FIG. 22 is a screenshot illustrating the display of the system when two aVF lead electrocardiographs are displayed in a dual pane view.
Figure 23:
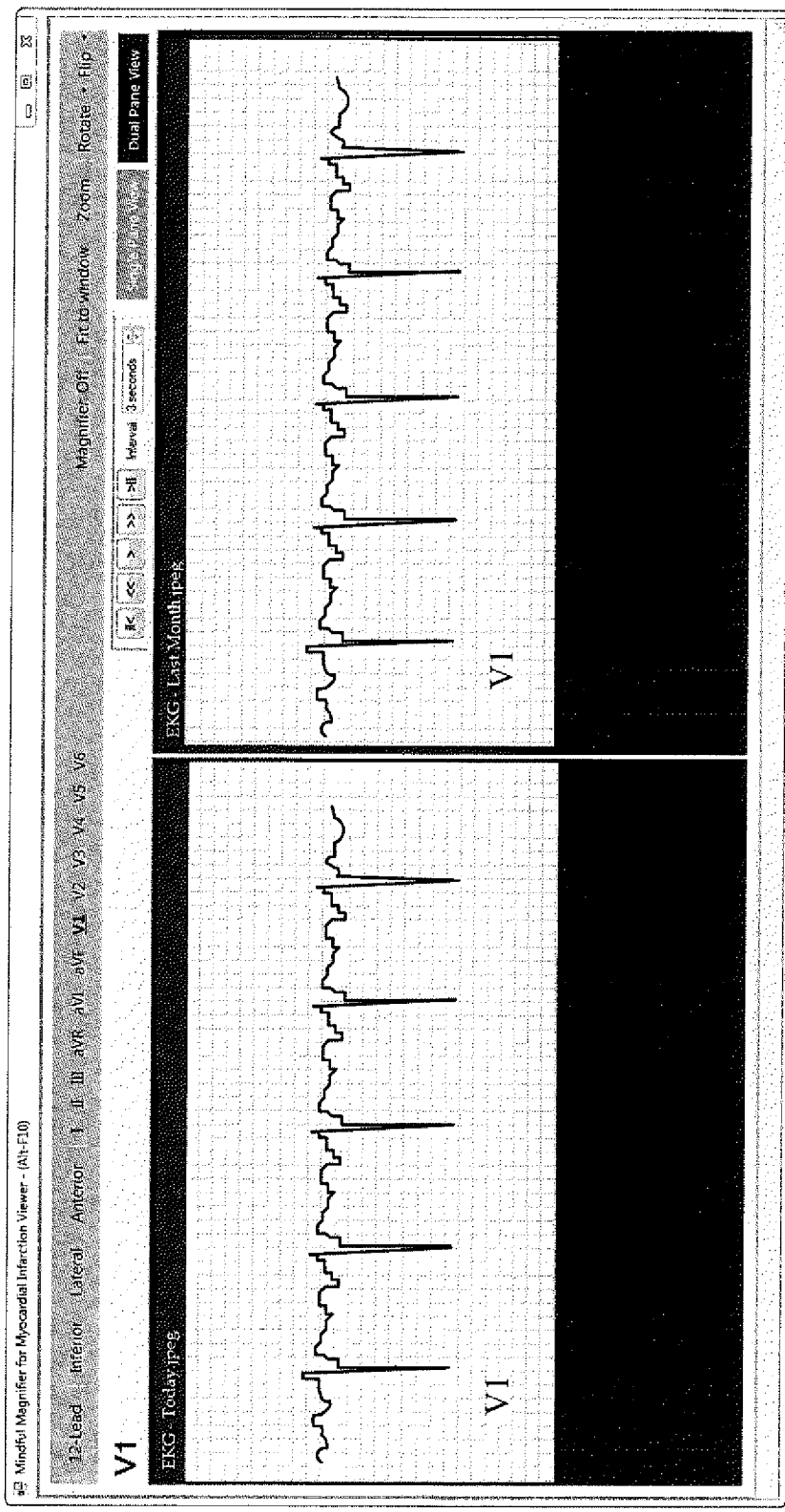
FIG. 23 is a screenshot illustrating the display of the system when two V1 lead electrocardiographs are displayed in a dual pane view.
Figure 24:
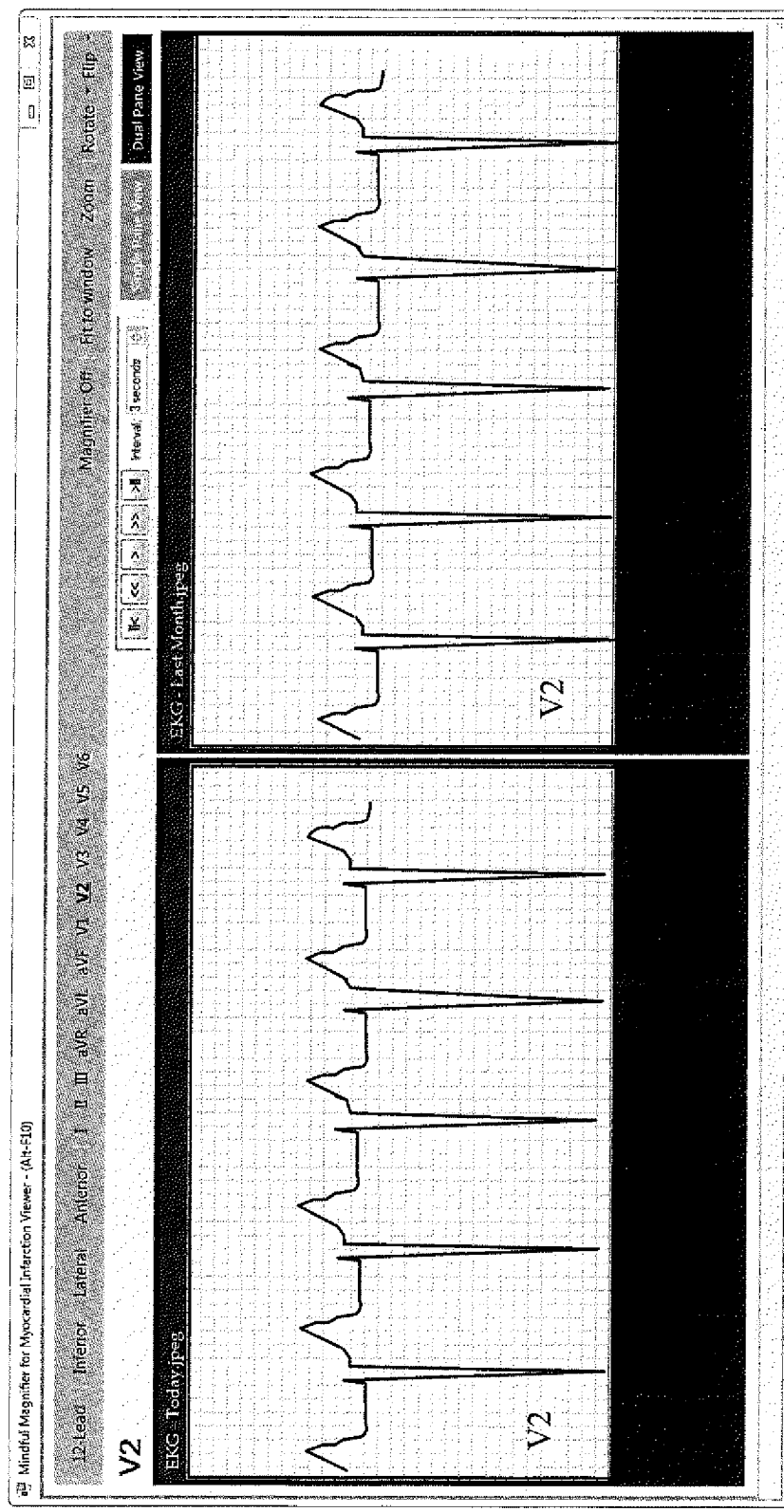
FIG. 24 is a screenshot illustrating the display of the system when two V2 lead electrocardiographs are displayed in a dual pane view.
Figure 25:
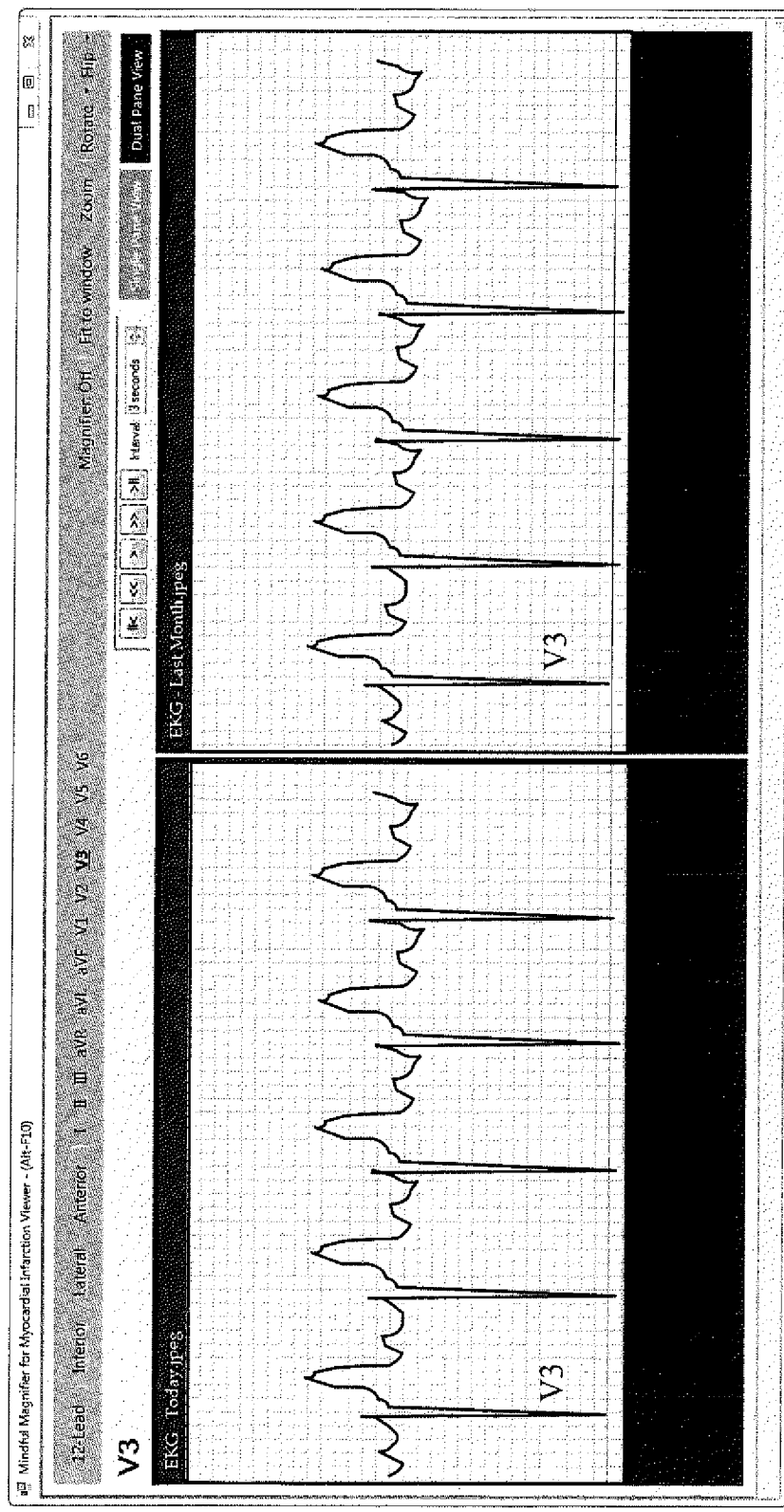
FIG. 25 is a screenshot illustrating the display of the system when two V3 lead electrocardiographs are displayed in a dual pane view.
Figure 26:
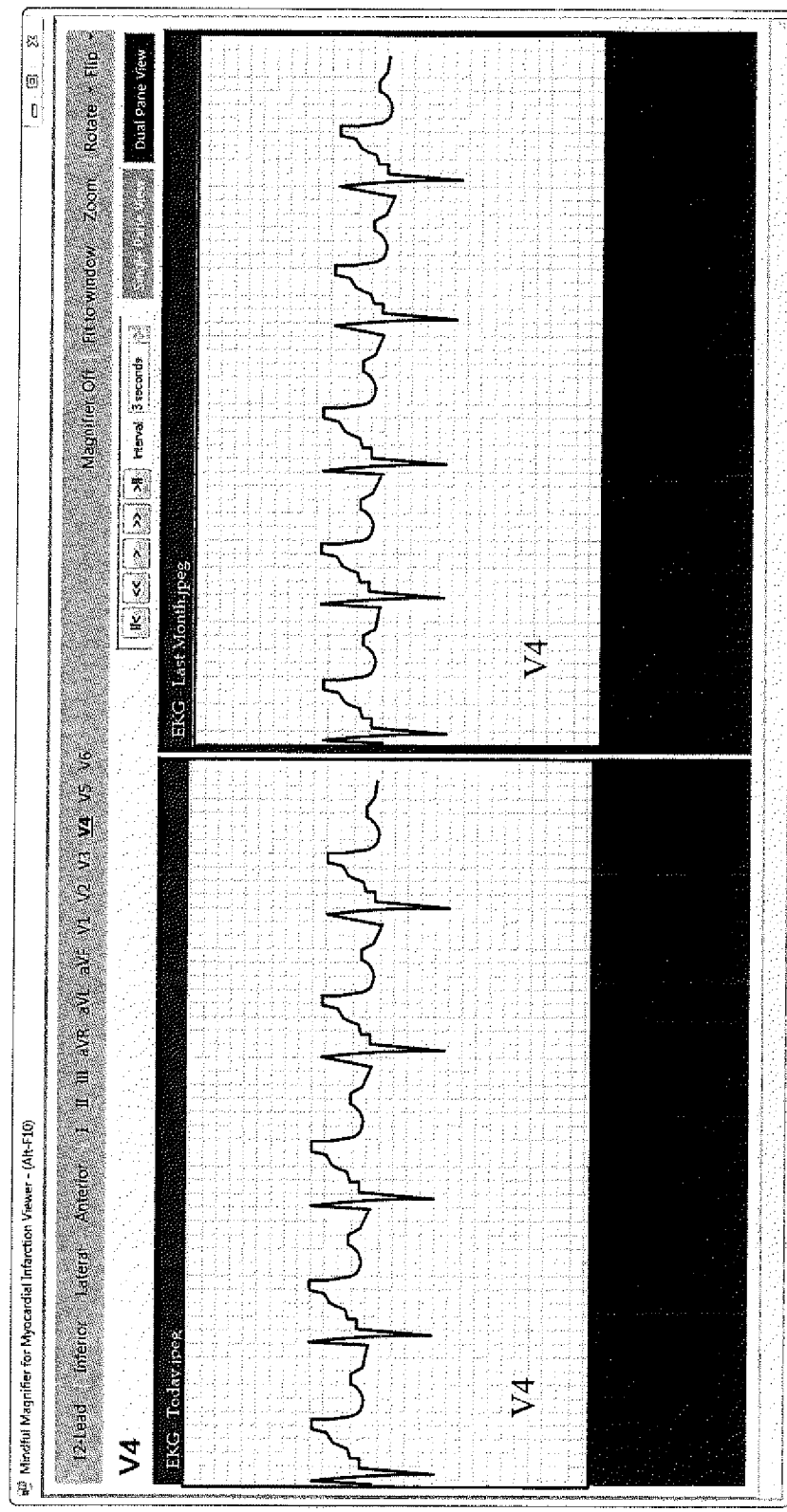
FIG. 26 is a screenshot illustrating the display of the system when two V4 lead electrocardiographs are displayed in a dual pane view.
Figure 27:
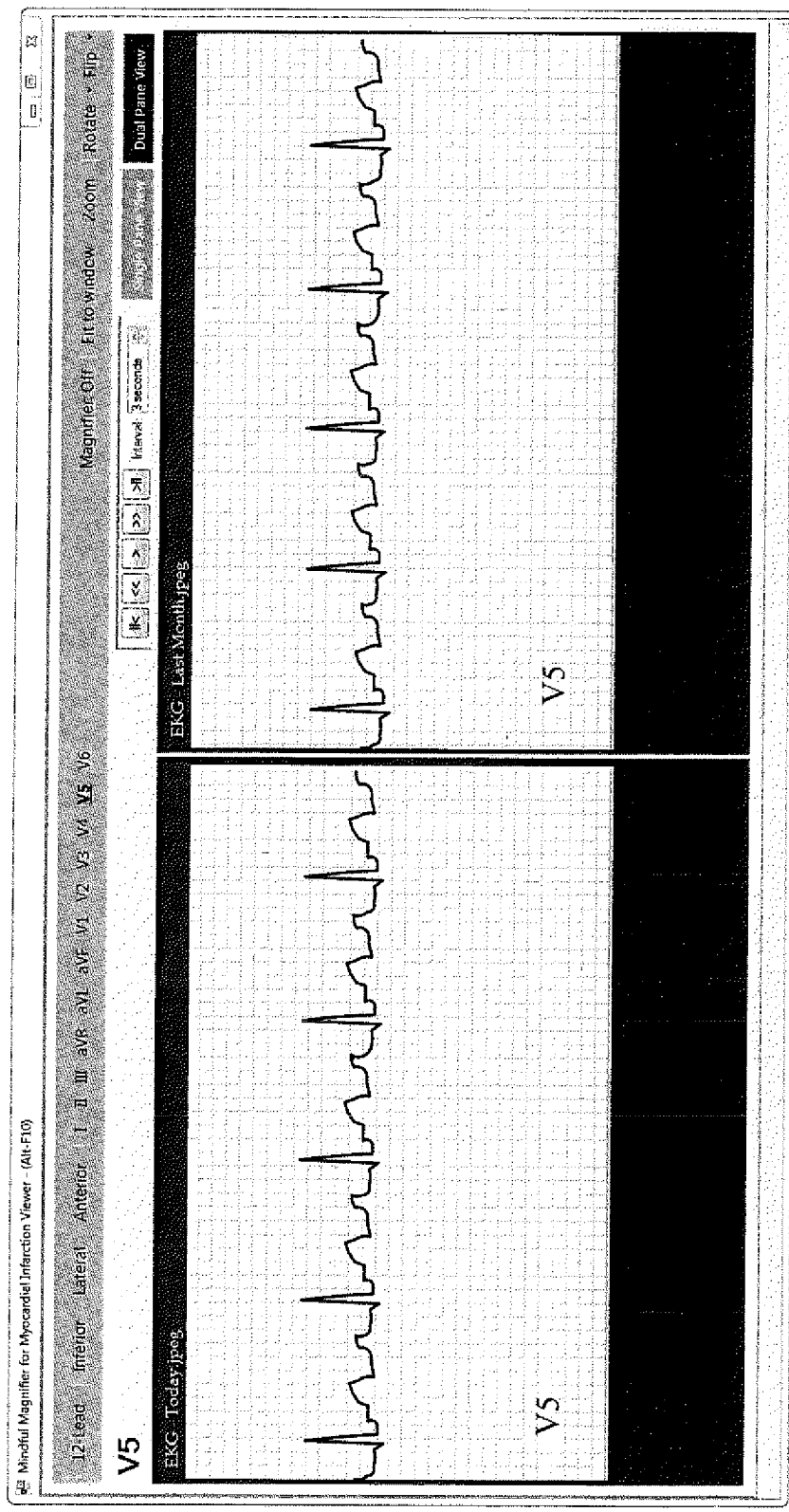
FIG. 27 is a screenshot illustrating the display of the system when two V5 lead electrocardiographs are displayed in a dual pane view.
Figure 28:
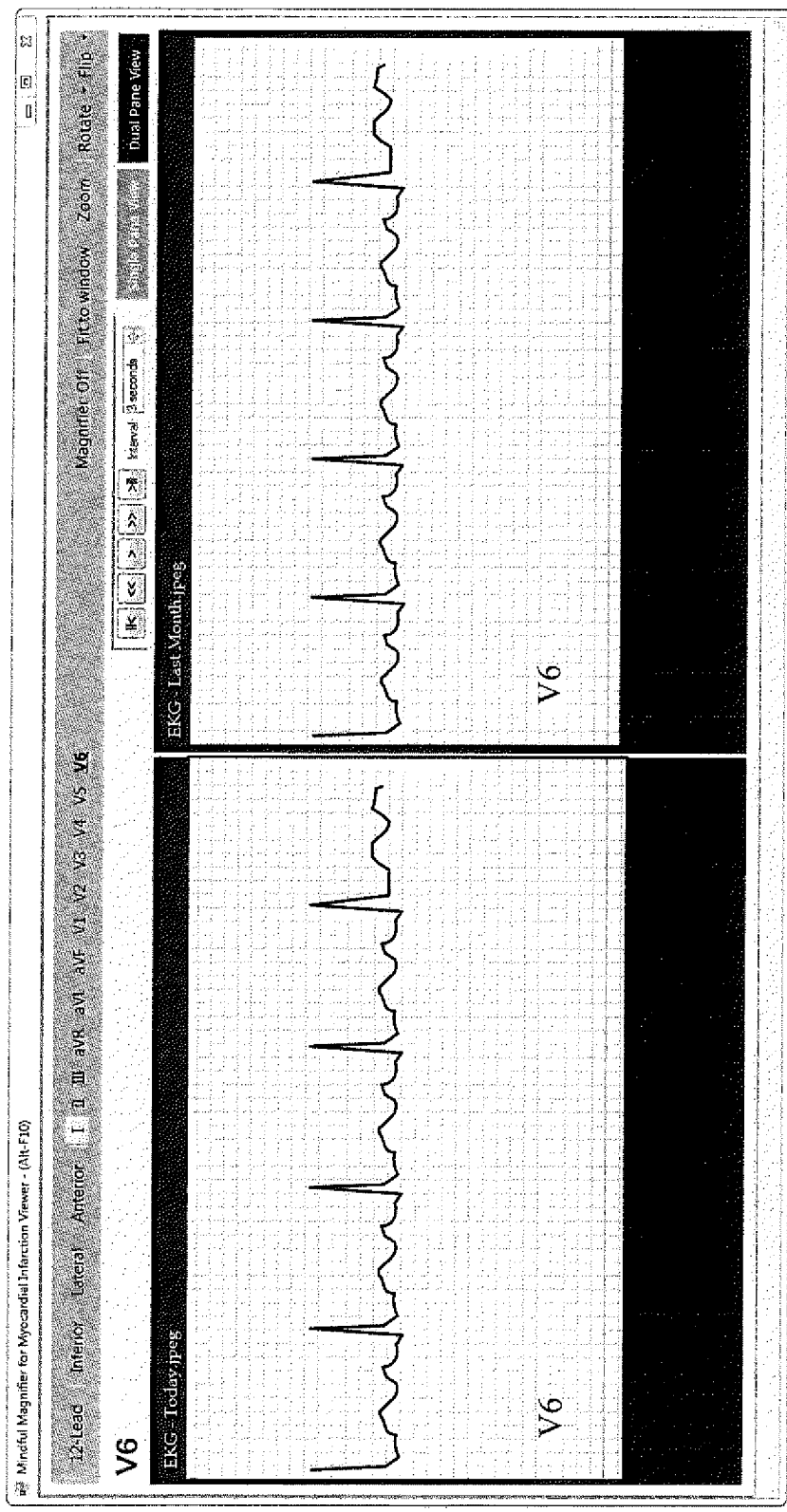
FIG. 28 is a screenshot illustrating the display of the system when two V6 lead electrocardiographs are displayed in a dual pane view.

An exemplary method of comparison is performed by placing electrographs side by side horizontally or vertically in a dual pane view, such as a previously collected electrocardiograph being placed next to, above, or below a current electrocardiograph. As explained above, the viewer can compare a full 12 lead electrocardiograph or tailor the display to a specific lead or heart wall. FIG. 16 provides an example dual pane view comparison of two complete 12 lead electrocardiographs, whereas FIGS. 17 through 28 show a side by side comparison of individual leads. FIG. 17 will be used as an example to more fully describe the dual pane comparison feature, as implemented on selected lead I. As illustrated in FIG. 17, a display 180 provides a visual comparison between today's ECG 182 and last month's ECG 184, where the lead I has been selected by the clinician from the list of available selections represented in toolbar 186. As shown in view selector 188, the comparison of two distinct electrocardiographs is presented in dual pane view. The system is further configured to provide various viewing tools as shown in menu 190.

For example, the dual pane view allows for specific portions of a lead to be magnified by the user. As described above with respect to the magnification capability of the system, the position and degree of the magnification can be controlled by the user to facilitate review of the electrocardiograph leads. Moreover, a user may select a single lead for display. Thus, an individual lead will fill a single pane view for independent analysis. A lead or multiple leads displayed on the screen can be further manipulated, independently or together, to aid in the clinician's analysis using the menu tools, such as rotate, zoom, flip, etc.

An additional means to compare the same element from two different electrocardiographs is to superimpose one electrocardiograph over the other electrocardiograph. In order to assess if the two electrocardiographs are different or the same in terms of the configuration of their shape, one of the leads may be highlighted and then presented over the other lead in a superimposed manner to see if the leads fit exactly, one over the other. This is especially useful in analyzing the ST segment or the T wave, in which case the assessment can be made as to whether there is a significant interval change between the two elements. If the leads do not superimpose well and a difference in height or width of the ST segment or T wave of the tracing is detected, then the conclusion can be made that an interval change has occurred between the two electrocardiographs with all the clinical significance that portends.

The system is further configured to identify any divergent portion of two superimposed electrocardiograph leads. As an example, a first lead can be colored yellow and a second lead can be colored blue. Portions of the two leads that overlap may take a green color, making areas of convergence readily apparent to the clinician. Additionally, portions where there is significant divergence may take yet another color such as red. Again, the reviewing clinician would immediately recognize areas of concern between the compared electrocardiographs. As some divergence is expected, the system can be configured to apply a threshold value above which a significant variance of data points in the superimposed electrocardiographs would result in identifying the area as one warranting greater scrutiny. In this example, the area may be colored red. Moreover, in areas of significant divergence, an additional alarm can be applied to draw the attention of the clinician to the abnormality. The alarm could be presented as a box containing text, an audio alert, a message that freezes the screen until the clinician acknowledges the alert, or any method suited to the display platform.

Multiple electrocardiographs can also be overlapped to aggregate statistical data and generate a graphical representation of the mean or median data points. This is particularly useful for a patient with a chronic condition requiring multiple electrocardiographs be performed.

Yet another method to compare multiple electrocardiographs is by simultaneously tracing the plotted graphs over the individual leads. For example, two leads can be displayed in a dual pane view, as shown in FIG. 17. Through an additional menu (not shown), a clinician can request a first node be positioned on one of the graphs, and the system can provide a second node on the other graph. The first and second nodes will represent the same distance from a common start point, such as a point on the graph representing the start time of the electrocardiograph. The system allows the clinician to freely place the node at a position of interest on a graph, employing any known method for interacting with a computer device, including, but not limited to, the use of a mouse, stylus, finger, voice activated commands, or textual input. As the clinician manipulates the node on a first electrocardiograph, the node on the second electrocardiograph will reflect the changed position of the node on the first electrocardiograph. Thus, a more complete and detailed visual analysis is provided to the clinician.

Further, as the node traces individual data points, information relating to that particular location on the lead can be presented in a header or independent patient information page (not shown).

Additionally, the node may follow the graph according to a set of rules as determined by a user. The rules can designate a portion of the electrocardiograph for the trace, a specific lead to be analyzed, or a specified time and speed for the trace feature. For example, a default setting may allow the clinician to initiate the trace program, where the first location of the node of both graphs is at a first time (e.g., when the test began). The nodes on the respective electrocardiographs would then progress simultaneously at a constant speed. To ensure that an area of concern is not overlooked, when the nodes reach a point where there is significant divergence, an alert can be presented to the user to draw attention to the abnormality in a fashion similar to the alert described above. For example, if the trace program is operating automatically, as the node reaches a data point with a significant divergence between the first and second electrocardiographs, the program may stop the node's progression and provide a text alert stating that an abnormality has been detected. The alert may also request or require a response acknowledging receipt of the alert from the user before the trace program can continue.

Figure 29:
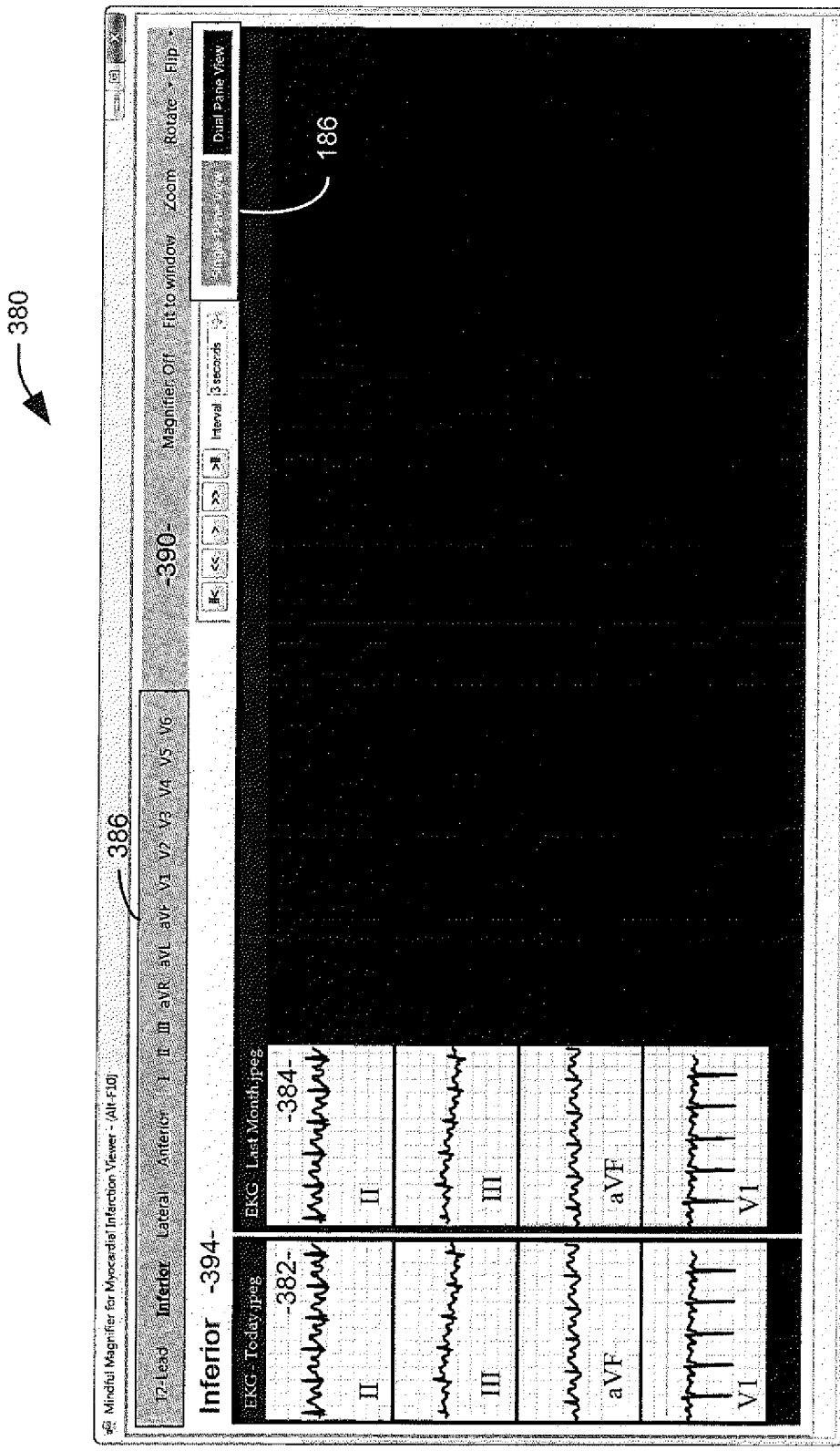
FIG. 29 is a screenshot illustrating the display of the system when only the set of leads representing the inferior wall of the heart are displayed in a dual pane view.
Figure 30:
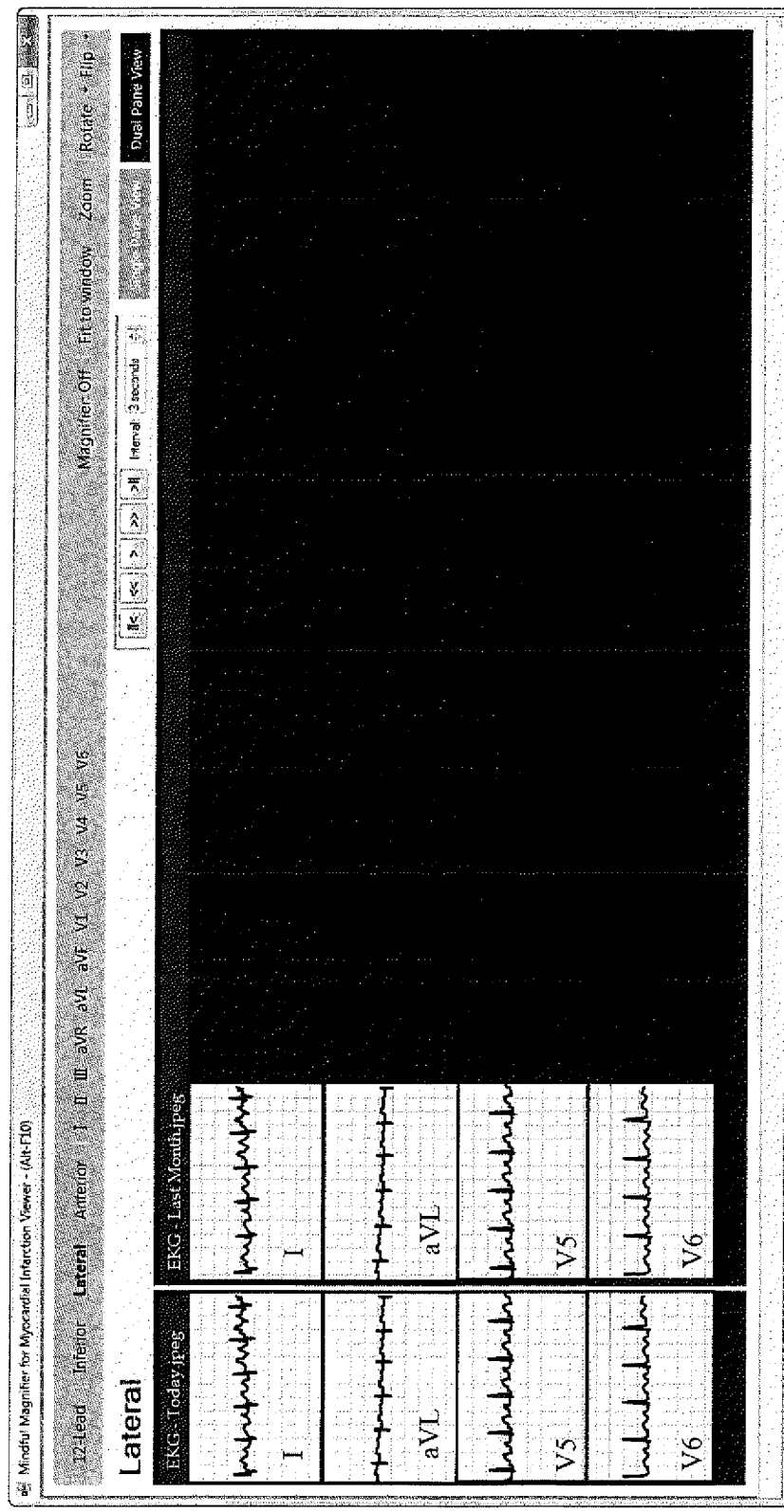
FIG. 30 is a screenshot illustrating the display of the system when only the set of leads representing the lateral wall of the heart are displayed in a dual pane view.
Figure 31:
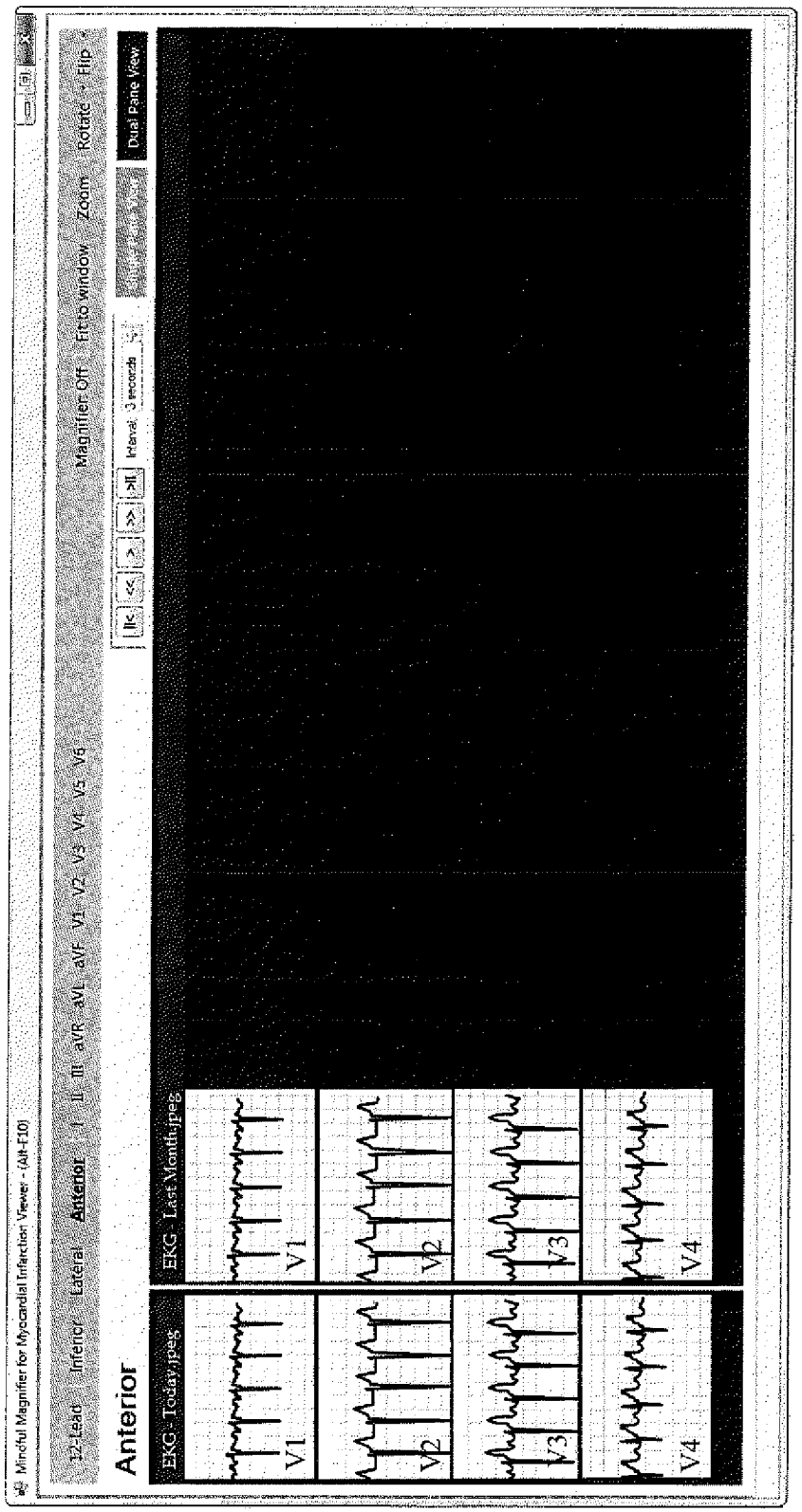
FIG. 31 is a screenshot illustrating the display of the system when only the set of leads representing the anterior wall of the heart are displayed in a dual pane view.

As yet another method to compare multiple electrocardiographs, a clinician can select a particular wall of the electrocardiograph for a focused analysis. As shown in FIG. 29, the inferior wall has been selected for independent display, as indicated in toolbar 386 and lead identifier 394. Accordingly, leads II, III, aVF and V1 associated with the inferior wall are displayed for each electrocardiograph 382 and 384. The system is configured to allow the displayed leads to be superimposed as described above. Further, the tracing method can be performed on one or more of the individual leads as instructed by a clinician using a menu and interactive tools described herein.

Figure 32:
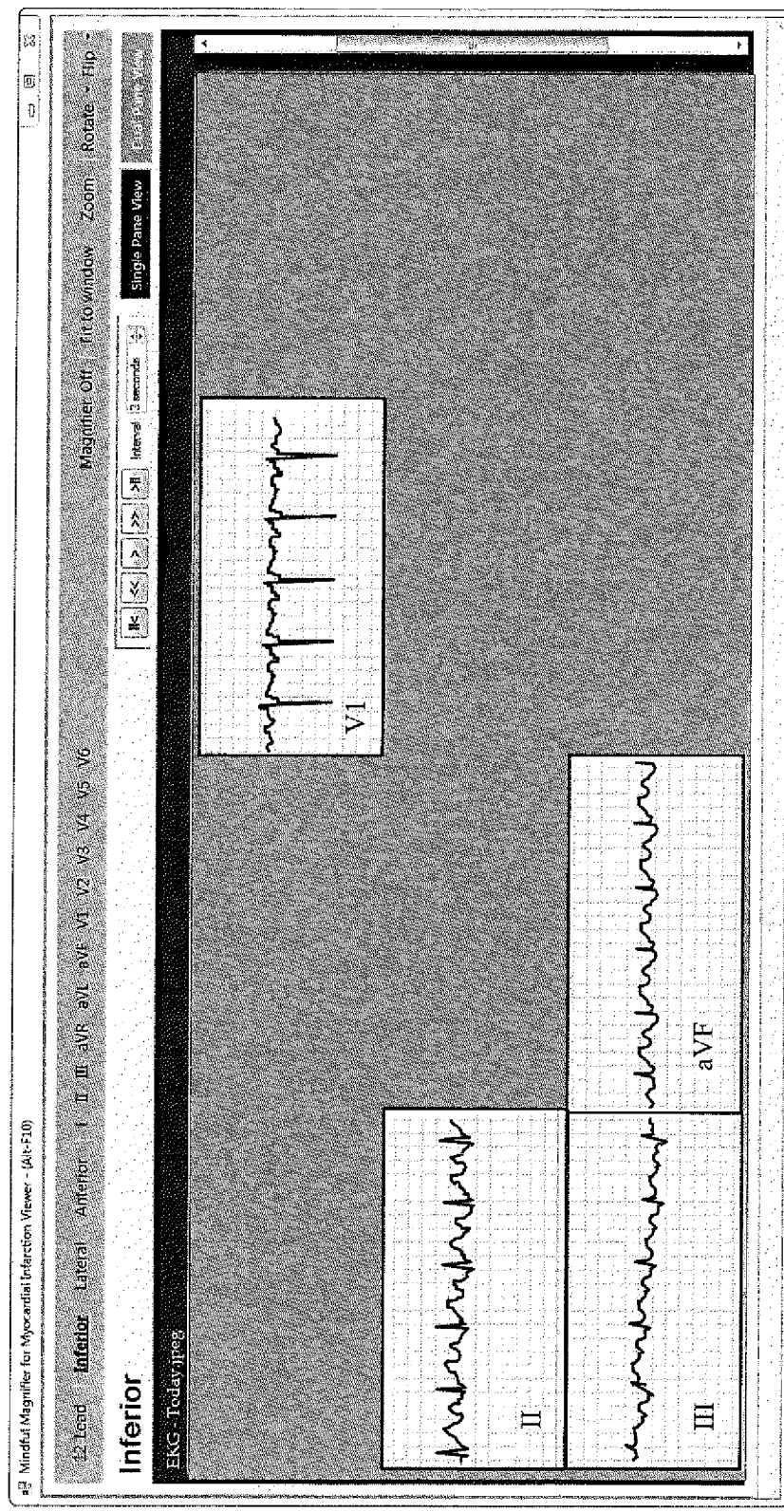
FIG. 32 is a screenshot illustrating the display of the system when only the set of leads representing the inferior wall of the heart are displayed.
Figure 33:
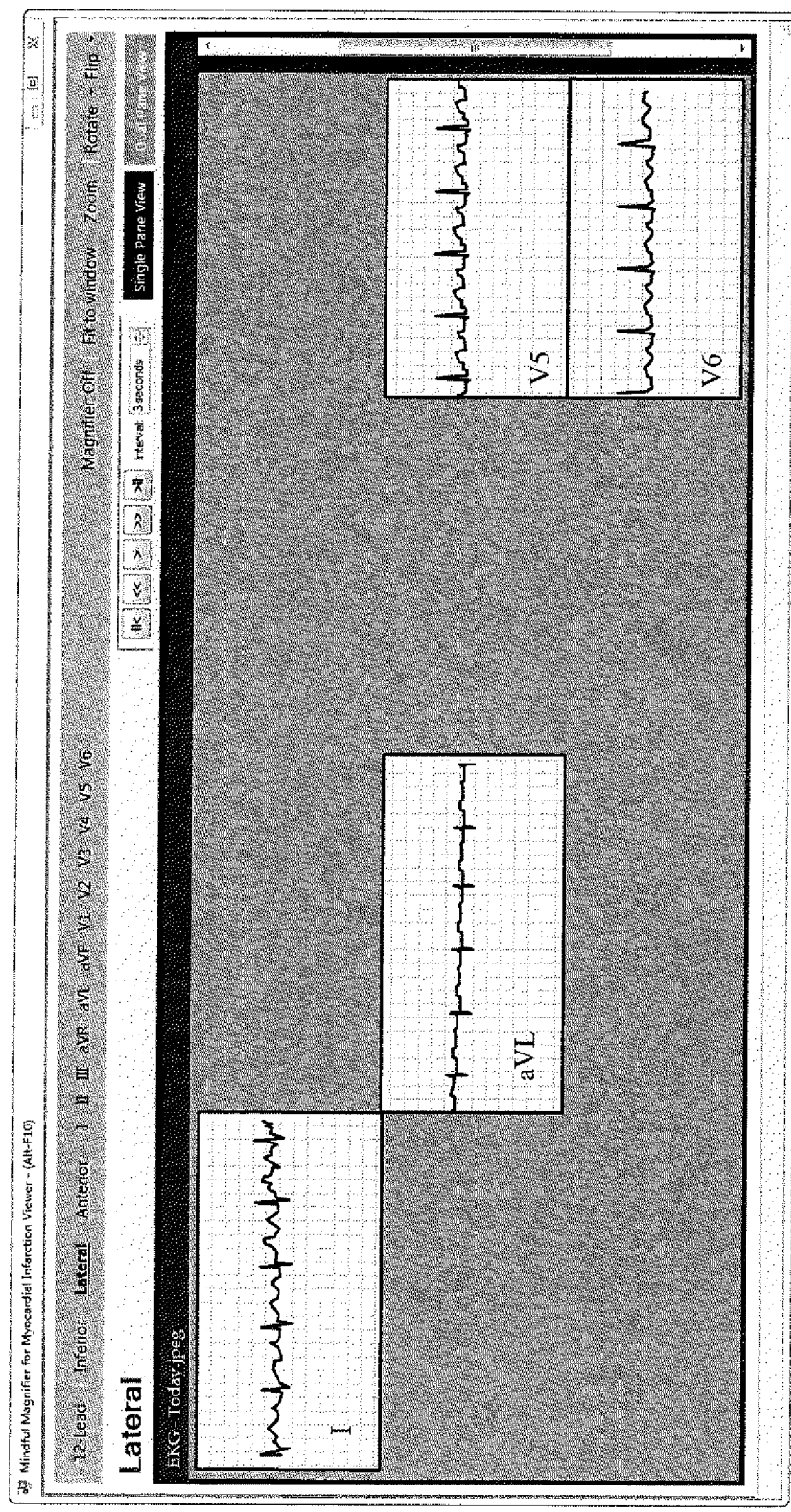
FIG. 33 is a screenshot illustrating the display of the system when only the set of leads representing the lateral wall of the heart are displayed.
Figure 34:
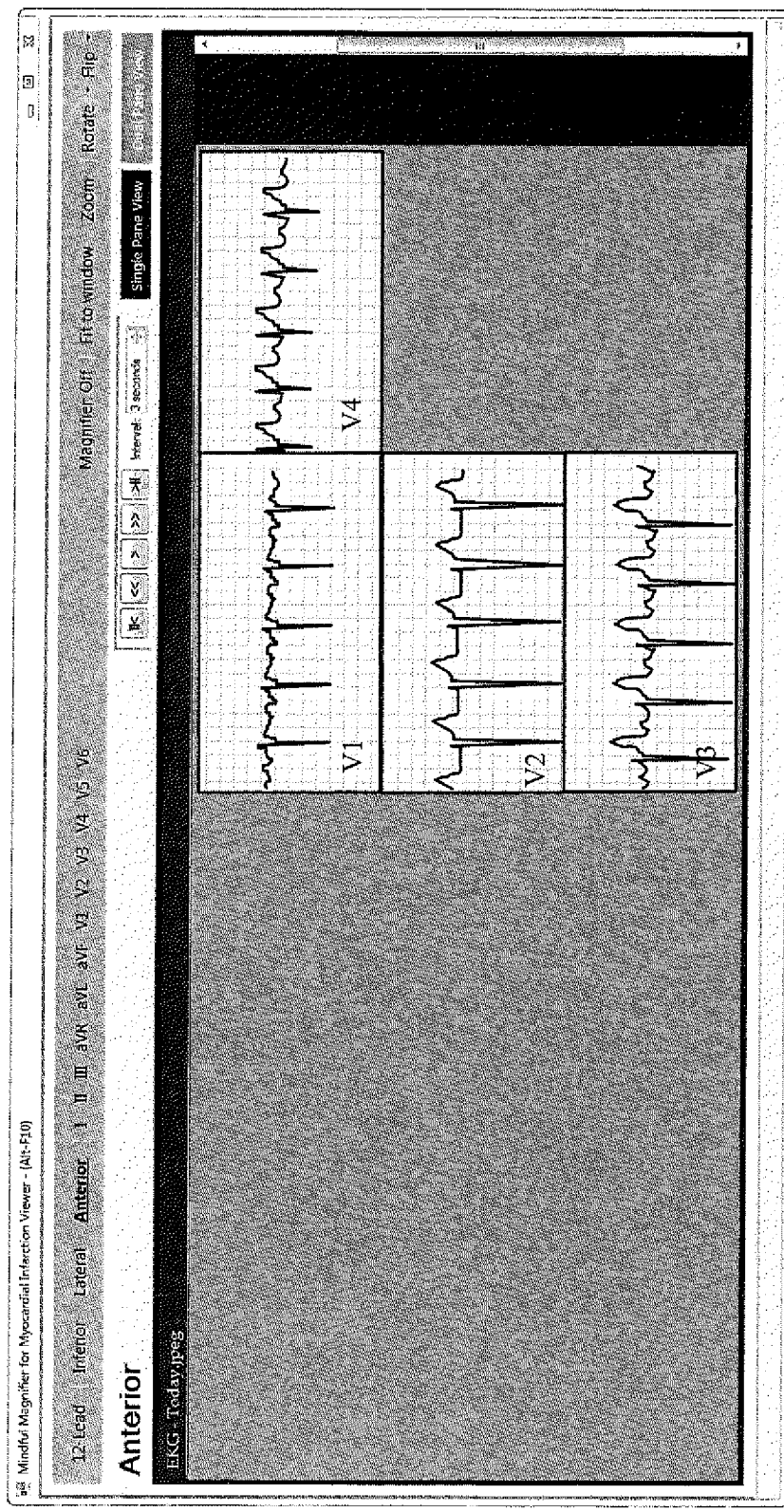
FIG. 34 is a screenshot illustrating the display of the system when only the set of leads representing the anterior wall of the heart are displayed.

Referencing FIGS. 32 to 34, a view pane containing a complete 12-lead electrocardiograph is configured to obscure the unselected portions of the 12-lead electrocardiograph to allow the clinician to focus attention on the selected information. Although examples have been described comparing two electrocardiographs, three or more electrocardiographs may be compared using the methods and devices described herein to yield similar results.

Figure 35:
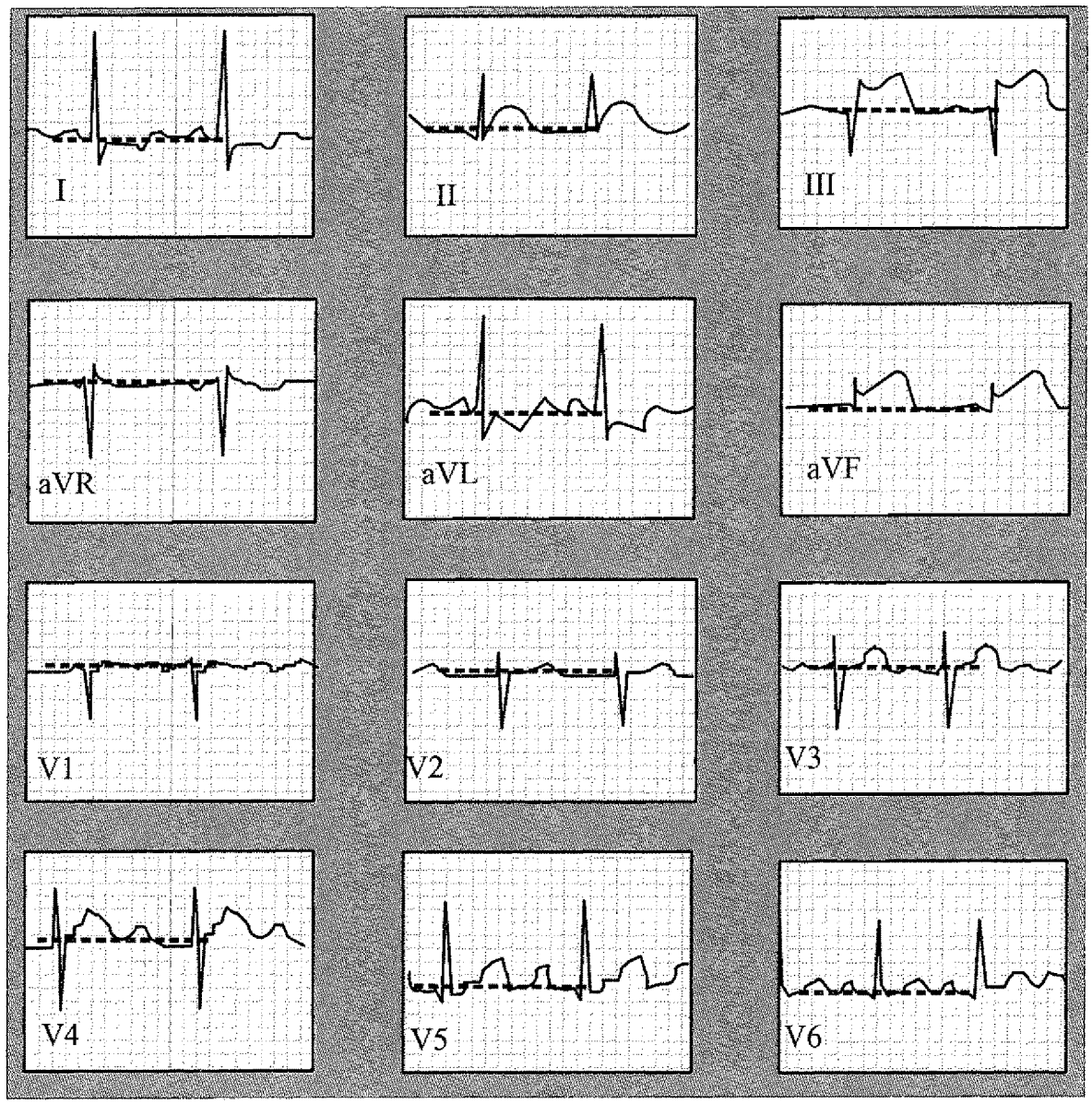
FIG. 35 is a screenshot illustrating the display of the system in which all twelve leads are displayed with an associated baseline.

Furthermore, FIG. 35 illustrates a screenshot 400 of the system in which all twelve leads are displayed with an associated baseline. It will be appreciated, however, that the leads can be displayed individually or in groups representing associated anatomical structures of the heart. As shown in FIG. 35, the system is capable of calculating a baseline for each lead, for example, from a cardiac cycle for a given patient or an average value (e.g., median or mean) for several cardiac cycles for the patient. As an example, the baseline 410 of lead I of an ECG is measured as the portion of the tracing following the T wave and preceding the next P wave and the segment between the P wave and the following QRS complex. In FIG. 35, the baseline 410 is shown as a horizontal dashed line on lead I. A similar baseline is also shown across each of the remaining leads. In a healthy heart, the baseline is equal to the isoelectric line and represents the periods in the cardiac cycle when there are no currents flowing towards either the positive or negative ends of the leads. However, in an abnormal heart, the baseline may be elevated (e.g. cardiac ischaemia) or depressed (e.g. myocardial infarction) relative to the isoelectric line.

The ST segment typically remains close to the isoelectric line as this is the period when no currents can flow in the ECG leads. Since most ECG recordings do not indicate where the line segment without electrical activity is located, baseline depression often gives the appearance of an elevation of the ST segment and conversely baseline elevation gives the appearance of depression of the ST segment. Accordingly, superimposing a baseline over a lead provides the viewer with a reference frame making recognition of a potentially abnormal condition quicker with less likelihood of misinterpretation, as is evident from FIG. 35.

Moreover, if the system identifies a deviation above or below the baseline that exceeds a predetermined threshold, an alert can be provided to a user or physician. For example, if the system calculates an ST segment variance as being elevated or depressed beyond an experimentally determined healthy level, or as compared against historical data for the patient being treated, the system can provide a visual or audio alert of the abnormal condition. For example, a range of values can be established from any of a number of recent cardiac cycles for the patient, historical data for the patient, or an average from a population of similar patients, and a user can be alerted any time the baseline falls outside of the established range.

Figure 36:
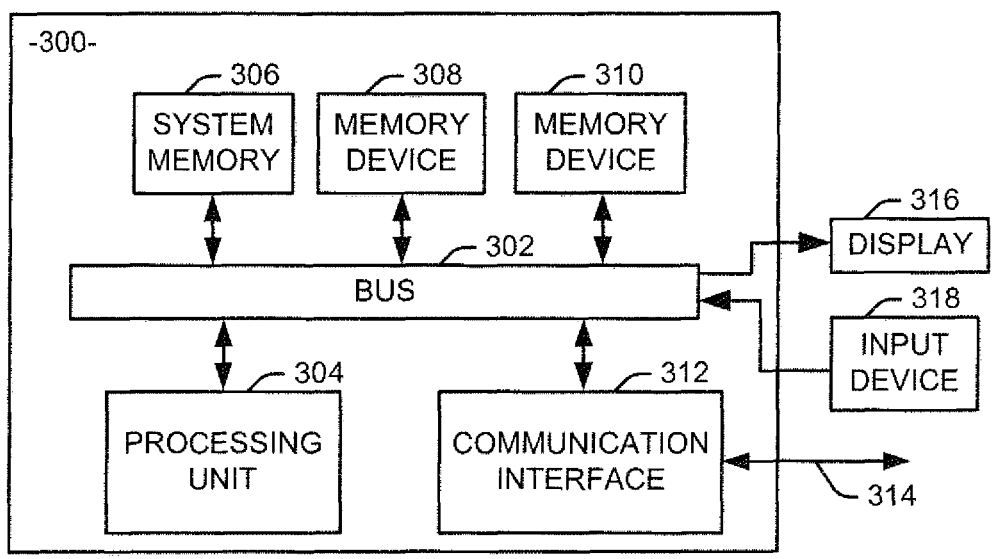
FIG. 36 is a schematic block diagram illustrating an exemplary system of hardware components capable of implementing examples of the present disclosed in FIGS. 1-35.

FIG. 36 is a schematic block diagram illustrating an exemplary system 300 of hardware components capable of implementing examples of the present disclosed in FIGS. 1-35, such as at least a portion of the display interface illustrated in FIG. 1. The system 300 can include various systems and subsystems. The system 300 can be a personal computer, a laptop computer, a workstation, a computer system, an appliance, an application-specific integrated circuit (ASIC), a server, a server blade center, a server farm, etc.

The system 300 can includes a system bus 302, a processing unit 304, a system memory 306, memory devices 308 and 310, a communication interface 312 (e.g., a network interface), a communication link 314, a display 316 (e.g., a video screen), and an input device 318 (e.g., a keyboard and/or a mouse). The system bus 302 can be in communication with the processing unit 304 and the system memory 306. The additional memory devices 308 and 310, such as a hard disk drive, server, stand alone database, or other non-volatile memory, can also be in communication with the system bus 302. The system bus 302 interconnects the processing unit 304, the memory devices 306-310, the communication interface 312, the display 316, and the input device 318. In some examples, the system bus 302 also interconnects an additional port (not shown), such as a universal serial bus (USB) port. The processing unit 304 can be a computing device and can include an application-specific integrated circuit (ASIC). The processing unit 304 executes a set of instructions to implement the operations of examples disclosed herein. The processing unit can include a processing core.

The additional memory devices 306, 308 and 310 can store data, programs, instructions, database queries in text or compiled form, and any other information that can be needed to operate a computer. The memories 306, 308 and 310 can be implemented as computer-readable media (integrated or removable) such as a memory card, disk drive, compact disk (CD), or server accessible over a network. In certain examples, the memories 306, 308 and 310 can comprise text, images, video, and/or audio, portions of which can be available in different human. Additionally, the memory devices 308 and 310 can serve as databases or data storage for system illustrated in FIG. 1. Additionally or alternatively, the system 300 can access an external data source through the communication interface 312, which can communicate with the system bus 302 and the communication link 314.

In operation, the system 300 can be used to implement a control system for an interactive overlay system that governs the interaction between the administrator and user. Computer executable logic for implementing the interactive overlay system resides on one or more of the system memory 306, and the memory devices 308, 310 in accordance with certain examples. The processing unit 304 executes one or more computer executable instructions originating from the system memory 306 and the memory devices 308 and 310. The term "computer readable medium" as used herein refers to a medium that participates in providing instructions to the processing unit 304 for execution, and can include multiple physical memory components linked to the processor via appropriate data connections.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. An electrocardiograph system comprising:
   a set of electrodes configured to detect a plurality of voltage differences between various pairs of locations on a body of a patient;
   a display configured to visually represent digital signals derived from the plurality of detected voltage differences; and
   a display interface configured to format the digital signals for the display, such that they are displayed as a sequence of proper subsets of the plurality of detected voltage differences, each proper subset of the plurality of detected voltage differences comprising leads representing a specific anatomical structure of a heart of the patient, the display interface configured to display the sequence of proper subsets of the plurality of detected voltage differences, such that each proper subset is displayed for at least a predetermined amount of time regardless of input from a user.

2. The electrocardiograph system of claim 1 further comprising a user interface configured to allow the user to manipulate the display of the sequence of proper subsets of the plurality of detected voltage differences by one of magnification, zooming, rotation, and flipping.

3. The electrocardiograph system of claim 1, wherein each proper subset of the plurality of detected voltage differences comprises leads representing one of an anterior wall, a lateral wall, an inferior wall, and a posterior wall of the heart of the patient.

4. The electrocardiograph system of claim 1 wherein the plurality of detected voltage differences is a given plurality of detected voltages, the system being configured to provide another plurality of detected voltages, the display interface configured to display the given and another plurality of detected voltages simultaneously.

5. The electrocardiograph system of claim 4 wherein the given plurality of detected voltages is displayed in one of juxtaposition and superimposition with another plurality of detected voltages.

6. A non-transitory computer readable medium storing machine executable instructions for displaying leads from an electrocardiograph, the machine executable instructions being executable by an associated computer to perform a method comprising:
   selecting a set of lead signals associated with one of the inferior, anterior, lateral, and posterior walls of the heart; and
   displaying the selected set of lead signals until at least a predetermined period of time has elapsed and an input is received from a user; and
      wherein the steps of selecting a set of lead signals and displaying the selected set of lead signals are repeated until respective sets of leads associated with each of the inferior, anterior, lateral, and posterior walls of the heart have been displayed.

7. A method for performing an electrocardiograph on a patient comprising:
   positioning a set of electrodes on the patient;
   processing a first set of voltage differences measured from the set of electrodes to provide a first plurality of lead signals representing activity of a heart of the patient;
   processing a second set of voltage differences measured from the set of electrodes to provide a second plurality of lead signals representing activity of a heart of the patient at a time different than a time associated with the first plurality of lead signals; and
   selectively displaying the lead signals such that proper subsets of the plurality of lead signals, each representing an anatomical structure of the heart, are displayed in sequence to an operator, such that each proper subset of the first plurality of lead signals is displayed with a corresponding proper subset of the second plurality of lead signals until at least a predetermined period of time has elapsed regardless of input from the operator.

8. The method of claim 7, wherein each proper subset of the plurality of lead signals comprises leads represents one of an anterior wall, a lateral wall, an inferior wall, and a posterior wall of the heart of the patient.

9. The method of claim 7, further comprising displaying a menu to allow a user to manipulate the display of the proper subsets of lead signals by one of magnification, zooming, rotation, and flipping.

* * * * *